United States Patent [19]
Schmidlin et al.

[11] Patent Number: 5,955,487
[45] Date of Patent: Sep. 21, 1999

[54] N-ACYL-N-HETEROCYCLYLALKYAMINO ACIDS COMPOSITIONS AND METHOD OF USE

[75] Inventors: Tibur Schmidlin, Basel; Paul Zbinden, Witterswil; Peter Bühlmayer, Arlesheim, all of Switzerland

[73] Assignee: Ciba-Geigy Corporation, Ardsley, N.Y.

[21] Appl. No.: 07/929,616

[22] Filed: Aug. 13, 1992

[30] Foreign Application Priority Data

Aug. 15, 1991 [CH] Switzerland ............................. 2405/91
Feb. 7, 1992 [CH] Switzerland ............................. 375/92
Apr. 8, 1992 [CH] Switzerland ............................. 1141/92

[51] Int. Cl.⁶ .......................... C07D 257/02; A61K 31/41
[52] U.S. Cl. ........................... 514/381; 548/253; 514/382
[58] Field of Search ..................... 514/381, 382; 548/253

[56] References Cited

FOREIGN PATENT DOCUMENTS 443983 2/1990 European Pat. Off. .
490820 12/1990 European Pat. Off. .
0411507 2/1991 European Pat. Off. ............... 548/243
429257 5/1991 European Pat. Off. ............... 548/469
434249 6/1991 European Pat. Off. .

OTHER PUBLICATIONS

Derwent Abstract 54175R (1970) of BE 745065–0.
Derwent Abstract 72453W/ (1974) of BE 827–777.
Derwent Abstract 91–134386 May 8, 1991 of EP 425,906.
Derwent Abstract 91–134402 May 1991 of EP 425,926.
Derwent Abstract 91–187155 Jun. 1991 of EP 434,365.
European Search Report dated Nov. 23, 1992.

Primary Examiner—Zinna Northington Davis
Attorney, Agent, or Firm—Irving M. Fishman; Karen G. Kaiser; Barbara J. Ikeler

[57] ABSTRACT

The invention relates to N-acyl-N-heterocyclylalkylamino acids of the formula

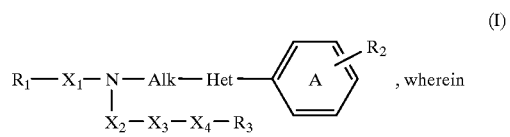

wherein $R_1$ is $C_1$–$C_7$alkyl that is unsubstituted or substituted by halogen or by hydroxy, or is $C_2$–$C_7$-alkenyl, $C_3$–$C_7$cycloalkyl, $C_3$–$C_7$cycloalkoxy, $C_1$–$C_7$alkoxy or $C_3$–$C_7$cycloalkyl-$C_1$–$C_7$alkoxy;

$R_2$ is 1H-tetrazol-5-yl, carboxy, $C_1$–$C_7$alkoxycarbonyl, $SO_3H$, $PO_2H_2$, $PO_3H_2$ or halo-$C_1$–$C_7$alkanesulfonylamino;

$R_3$ is 1H-tetrazol-5-yl, hydroxymethyl, $C_1$–$C_7$alkoxymethyl, formyl, carboxy, $C_1$–$C_7$alkoxycarbonyl, $C_1$–$C_7$alkoxy-$C_1$–$C_7$alkoxycarbonyl, phenyl-$C_1$–$C_4$alkoxycarbonyl or carbamoyl, the amino group of which is unsubstituted or mono-substituted by $C_1$–$C_7$alkyl, $C_3$–$C_7$alkenyl or by phenyl-$C_1$–$C_7$alkyl or di-substituted by $C_1$–$C_7$alkyl, $C_3$–$C_7$alkenyl or by phenyl-$C_1$–$C_7$alkyl independently of one another, or is di-substituted by $C_2$–$C_7$alkylene or by $C_2$–$C_4$alkyleneoxy-$C_2$–$C_4$alkylene;

Alk is methylene, ethylene or ethylidene;

and their salts; preparation processes, pharmaceutical compositions comprising a compound of formula I or a pharmaceutically acceptable salt thereof, and use.

12 Claims, No Drawings

N-ACYL-N-HETEROCYCLYLALKYAMINO ACIDS COMPOSITIONS AND METHOD OF USE

The invention relates to N-acyl-N-heterocyclylalkylamino acids of the formula

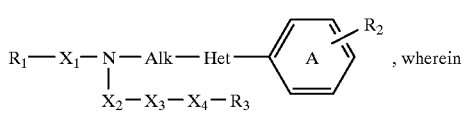, wherein (I)

$R_1$ is $C_1$–$C_7$alkyl that is unsubstituted or substituted by halogen or by hydroxy, or is $C_2$–$C_7$alkenyl, $C_3$–$C_7$cycloalkyl, $C_3$–$C_7$cycloalkoxy, $C_1$–$C_7$alkoxy or $C_3$–$C_7$cycloalkyl-$C_1$–$C_7$-alkoxy;

$R_2$ is 1H-tetrazol-5-yl, carboxy, $C_1$–$C_7$alkoxycarbonyl, $SO_3H$, $PO_2H_2$, $PO_3H_2$ or halo-$C_1$–$C_7$alkanesulfonylamino;

$R_3$ is 1H-tetrazol-5-yl, hydroxymethyl, $C_1$–$C_7$alkoxymethyl, formyl, carboxy, $C_1$–$C_7$alkoxycarbonyl, $C_1$–$C_7$alkoxy-$C_1$–$C_7$alkoxycarbonyl, phenyl-$C_1$–$C_4$alkoxycarbonyl or carbamoyl, the amino group of which is unsubstituted or mono-substituted by $C_1$–$C_7$alkyl, $C_3$–$C_7$alkenyl or by phenyl-$C_1$–$C_7$alkyl or di-substituted by $C_1$–$C_7$alkyl, $C_3$–$C_7$alkenyl or by phenyl-$C_1$–$C_7$alkyl independently of one another, or is di-substituted by $C_2$–$C_7$alkylene or by $C_2$–$C_4$alkyleneoxy-$C_2$–$C_4$alkylene;

Alk is methylene, ethylene or ethylidene;

Het is

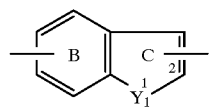 (i)

wherein $Y_1$ is O, S or N(R) and R is hydrogen or $C_1$–$C_7$alkyl; or

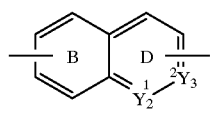 (ii)

wherein one of the variables $Y_2$ is $Y_3$ is C(R') and the other is N or each of the variables is C(R'); and R' is hydrogen, halogen, $C_1$–$C_7$alkyl, $C_1$–$C_7$alkoxy, $C_2$–$C_7$alkenyloxy, phenoxy, benzyloxy, trifluoromethyl or $S(O)_m$—R, wherein m is 0, 1 or 2; and R is hydrogen or $C_1$–$C_7$alkyl;

$X_1$ is —CO— or —$S(O)_m$— and the index m is 0, 1 or 2; one of the variables $X_2$ and $X_4$ is $C_1$–$C_4$alkylene and the other of the variables $X_2$ and $X_4$ is a bond; or each of the variables $X_2$ and $X_4$ is a bond;

$X_3$ is $C_3$–$C_7$cycloalkylidene or the structural element —C($X_a$)($X_b$)— and $X_a$ is hydrogen or $C_1$–$C_7$alkyl and $X_b$ is $C_1$–$C_7$alkyl;

and the rings A, B, C and D, with the exception of the substituents indicated in the formula, and also aromatic substituents are, independently of one another, unsubstituted or mono- or poly-substituted by substituents selected from the group consisting of halogen, $C_1$–$C_7$alkyl, $C_1$–$C_7$alkoxy, $C_2$–$C_7$alkenyloxy, phenoxy, benzyloxy, trifluoromethyl and $S(O)_m$—R, wherein m is 0, 1 or 2 and R is hydrogen or $C_1$–$C_7$alkyl;

and their salts; preparation processes, pharmaceutical compositions comprising a compound of formula I or a pharmaceutically acceptable salt thereof, and use.

The compounds I may be in the form of salts, especially pharmaceutically acceptable salts. If the compounds I have at least one basic centre, they can form acid addition salts. These are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$–$C_4$alkane-carboxylic acids, for example acetic acid, such as unsaturated or saturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as unsubstituted or substituted, for example halo-substituted $C_1$–$C_4$alkane- or aryl-sulfonic acids, for example methane- or p-toluene-sulfonic acid. Corresponding acid addition salts can also be formed with any additional basic centre which may be present. Furthermore, compounds I having at least one acidic group (for example COOH or 1H-tetrazol-5-yl) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropyl-amino, or a mono-, di- or tri-hydroxy-lower alkylamine, for example mono, di- or tri-ethanolamine. In addition, depending on the acid and base strength of the corresponding groups, internal salts may be formed. Also included are salts that are not suitable for pharmaceutical use but which can be used, for example, for the isolation or purification of free compounds I or the pharmaceutically acceptable salts thereof.

The rings A, B, C and D, with the exception of the substituents indicated in the formula. and also aromatic substituents, such as phenoxy or benzyloxy, are, independently of one another, unsubstituted or mono-substituted or, less preferably, poly-substituted, for example di- or tri-substituted, by substituents selected from the group consisting of halogen, $C_1$–$C_7$alkyl, $C_1$–$C_7$alkoxy, $C_2$–$C_7$alkenyloxy, phenoxy, benzyloxy, trifluoromethyl and $S(O)_m$—R, wherein the index m is 0, 1 or 2 and R is hydrogen or $C_1$–$C_7$alkyl.

Het is benzofuran, benzo[b]thiophene, indole, quinoline and isoquinoline. Het is also naphthalene. If Het is

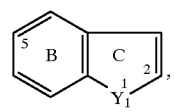,

Het is linked to Alk via position 4, 6 or 7, but especially via position 5, and to the phenyl ring A via position 3, but especially via position 2. Accordingly, the ring C can have a maximum of one further substituent. If Het is

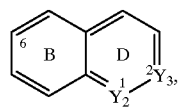

Het is linked to Alk via positions 5, 7 or 8, but especially via positions 6, and to the phenyl ring A, for example, via positions 3 or 4, but especially via position 2($Y_3$=CR'). If $Y_2$ or $Y_3$ is CH (that is to say, R' is hydrogen), the phenyl ring A can be linked to the ring D via $Y_2$ or, especially, via $Y_3$.

Preferred Het is

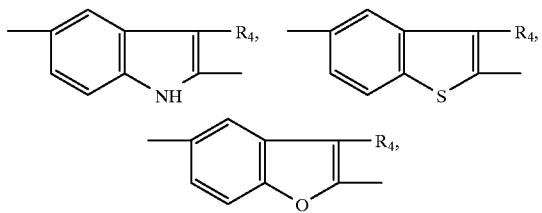

wherein $R_4$ is hydrogen, halogen, $C_1$–$C_7$alkyl, $C_1$–$C_7$alkoxy, $C_2$–$C_7$alkenyloxy, phenoxy, benzyloxy, trifluoromethyl or $S(O)_m$—R, wherein m is 0, 1 or 2 and R is hydrogen or$C_1$–$C_7$alkyl. Preferred $R_4$ is hydrogen, halogen, such as bromine, also $C_1$–$C_7$alkyl, $C_1$–$C_7$alkoxy or trifluoromethyl; Het is especially

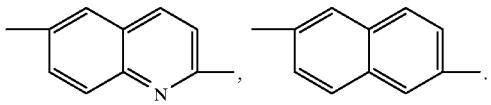

Compounds of formula I, for example those in which Alk is ethylidene or in which $X_a$ and $X_b$ have different meanings, may, depending on the number and absolute and relative configuration of the asymmetric carbon atoms, be in the form of pure isomers, such as antipodes and/or diastereoisomers, or in the form of isomeric mixtures, such as enantiomeric mixtures, for example racemates, diastereoisomeric mixtures or racemate mixtures; the present invention relates also to corresponding forms.

The general terms used hereinbefore and hereinafter have the following meanings, unless defined otherwise.

The term "lower" means that corresponding groups and compounds have from 1 up to and including 7, preferably from 1 up to and including 4, carbon atoms.

$C_1$–$C_7$alkyl is, for example, methyl, ethyl, n-propyl, isopropyl, n-butyl, isobutyl, sec-butyl, tert-butyl or a corresponding pentyl, hexyl or heptyl radical, $C_1$–$C_4$alkyl is preferred.

$C_1$–$C_7$alkyl that is substituted by halogen contains one or more halogen atom(s) and is, for example, trifluoromethyl, 2-chloro-1,1,2-trifluoroethyl, chloromethyl, 3,3,3-trifluoropropyl, 4-chlorobutyl or heptafluoropropyl. Halo-$C_1$–$C_4$alkyl is preferred.

$C_1$–$C_7$alkyl that is substituted by hydroxy is especially mono-substituted by hydroxy and is, for example, hydroxymethyl, 2-hydroxyethyl, 3-hydroxypropyl or 4-hydroxybutyl. Hydroxy-$C_1$–$C_4$alkyl is preferred.

$C_2$–$C_7$alkenyl is, for example, vinyl, propen-2-yl, allyl or but-1-en-3-yl, -1-en-4-yl, -2-en-1-yl or -2-en-2-yl. $C_3$–$C_7$alkenyl, especially $C_3$–$C_5$alkenyl, is preferred.

$C_3$–$C_7$cycloalkyl is cyclopropyl, cyclobutyl, cyclopentyl, cyclohexyl or cycloheptyl. Cyclopropyl is preferred.

$C_3$–$C_7$cycloalkoxy is cyclopropoxy, cyclobutoxy, cyclopentyloxy, cyclohexyloxy or cycloheptyloxy. Cyclopropoxy and cyclopentyloxy are preferred.

$C_1$–$C_7$alkoxy is, for example, methoxy, ethoxy, n-propoxy, isopropoxy, n-butoxy, sec-butoxy or tert-butoxy or corresponding pentyloxy, hexyloxy or heptyloxy. $C_1$–$C_4$alkoxy is preferred.

$C_3$–$C_7$cycloalkyl-$C_1$–$C_7$alkoxy is, for example, $C_3$–$C_7$cycloalkyl-$C_1$–$C_2$alkoxy, such as cyclopropyl-methoxy or -ethoxy, cyclobutyl-methoxy or -ethoxy, cyclopentyl-methoxy or -ethoxy, cyclohexyl-methoxy or -ethoxy or cycloheptyl-methoxy or -ethoxy. Cyclopropyl-methoxy is preferred.

$C_1$–$C_7$alkoxycarbonyl is, for example, methoxy-, ethoxy-, n-propoxy-, isopropoxy-, n-butoxy- or tert-butoxy-carbonyl. $C_1$–$C_4$alkoxycarbonyl is preferred.

Halogen is especially halogen having an atomic number of up to and including 35, that is to say, fluorine, chlorine or bromine, and also includes iodine.

Halo-$C_1$–$C_7$alkanesulfonylamino is, for example, trifluoromethane-, difluoromethane-, 1,1,2-trifluoroethane- or heptafluoropropane-sulfonylamino. Halo-$C_1$–$C_4$alkanesulfonyl-amino is preferred.

$C_1$–$C_7$alkoxy-$C_1$–$C_7$alkoxycarbonyl is, especially, $C_1$–$C_4$alkoxy$C_1$–$C_4$alkoxycarbonyl, such as 2-methoxyethoxycarbonyl, 2-ethoxyethoxycarbonyl, 3-methoxypropoxycarbonyl or 3-ethoxypropoxycarbonyl.

Phenyl-$C_1$–$C_4$alkoxycarbonyl is, especially, benzyloxy- or 1- or 2-phenylethoxy-carbonyl. Phenyl-$C_1$–$C_2$alkoxycarbonyl is preferred.

Phenyl-$C_1$–$C_7$alkyl is, for example, benzyl or 1- or 2-phenethyl. Phenyl-$C_1$–$C_4$alkyl is especially preferred.

$C_2$–$C_7$alkylene is straight-chained or branched and is, especially, eth-1,2-ylene, prop-1,3-ylene, but-1,4-ylene, pent-1,5-ylene, prop-1,2-ylene, 2-methylprop-1,3-ylene or 2,2-dimethylprop-1,3-ylene. $C_2$–$C_5$alkylene is preferred.

$C_2$–$C_4$alkyleneoxy is, for example, allyloxy, but-2-en-1-yloxy or but-3-en-1-yloxy.

$C_2$–$C_4$alkyleneoxy-$C_2$–$C_4$alkylene is preferably ethyleneoxyethylene.

$C_1$–$C_4$alkylene is, for example, methylene, ethylene, propylene or butylene.

$C_3$–$C_7$cycloalkylidene is cyclopropylidene, cyclobutylidene, cyclopentylidene, cyclohexylidene or cycloheptylidene. Cyclopentylidene and cyclohexylidene are preferred.

$C_2$–$C_7$alkenyloxy is, for example, allyloxy or but-2-en- or but-3-en-yloxy; $C_3$–$C_5$alkenyloxy is preferred.

Preferably, unsaturated radicals are not bonded by way of the atom from which the multiple bond extends.

Extensive pharmacological studies have shown that the compounds I and their pharmaceutically acceptable salts have, for example, pronounced angiotensin II-antagonising properties.

It is known that angiotensin II has strong vasoconstrictive properties and also stimulates aldosterone secretion and thus causes pronounced sodium/water retention. The result of angiotensin II activity is manifested, inter alia, in an increase in blood pressure.

The importance of angiotensin II-antagonists resides in the fact that, by competitive inhibition of the binding of angiotensin II to the receptors, they suppress the vasoconstrictive and aldosterone secretion-stimulating effects caused by angiotensin II.

The angiotensin II-antagonising properties of the compounds I and their pharmaceutically acceptable salts can be demonstrated in the angiotensin II binding test. In that test, smooth-muscle cells of rats obtained from the homogenised aorta of rats are used. The solid centrifuge is suspended in 50 mM of Tris buffer (pH 7.4) using peptidase inhibitors. The samples are incubated for 60 minutes at 25° C. with $^{125}$I-angiotensin II (0.175 nM) and a varying concentration of angiotensin II or of test compound. Incubation is then stopped by the addition of sodium chloride buffered with ice-cold phosphate and filtration is carried out through Whatman GF/F filters. The γ-radiation activity of the filters is counted using a gamma-counter. The $IC_{50}$ values are determined from the dose-effect curve. $IC_{50}$ values of approximately 10 nM and above are determined for the compounds I and their pharmaceutically acceptable salts.

Studies of the isolated aortic ring of rabbits can be used to determine angiotensin II-induced vasoconstriction. For that purpose, aortic rings are prepared from each side of the thorax and secured between two parallel clips with an initial tension of 2 g. The rings are then immersed in 20 ml of a tissue bath at 37° C. and gassed with a mixture of 95% $O_2$ and 5% $CO_2$. The isometric reactions are measured. The rings are alternately stimulated with 10 mM angiotensin II (Hypertensin-CIBA) and 5 nM noradrenalin chloride at 20-minute intervals. The rings are then incubated with selected concentrations of the test compounds prior to treatment with the agonists. The data are analysed using a Buxco digital computer. The concentrations that bring about 50% inhibition of the initial control values are indicated as $IC_{50}$ values. $IC_{50}$ values of approximately 10 nM and above are determined for the compounds I and their pharmaceutically acceptable salts.

The fact that the compounds I and their pharmaceutically acceptable salts can reduce high blood pressure induced by angiotensin II can be verified in the test model of the normotensive, narcotised and despinalised rat. Two hours after treatment with the test compound, the rat is narcotised and the blood pressure is measured directly in the carotid artery and recorded using an on-line data recording system (Buxco). Noradrenalin (1 μg/kg i.v.) and angiotensin II (0.4 μg/kg i.v.) are administered intravenously by bolus injection. The specificity of the angiotensin II-antagonism is indicated by the selective inhibition of the pressure effect induced by angiotensin II but not of that induced by noradrenalin. In this test model, the compounds I and their pharmaceutically acceptable salts exhibit an inhibiting effect at a dose of approximately 3 mg/kg p.o. and above.

The antihypertensive activity of the compounds I and their pharmaceutically acceptable salts can also be demonstrated in the test model of the renally hypertensive rat. High blood pressure is produced in male rats by constricting a renal artery in accordance with the Goldblatt method. Doses of the test compound are administered to the rats using a stomach tube. Control animals receive an equivalent volume of solvent. The blood pressure and heartbeat are measured indirectly on conscious animals in accordance with the tail-clamping method of Gerold et al. [*Helv. Physiol. Acta* 24 (1966), 58] before administering the test compound or the solvent and also at intervals during the course of the experiments. The pronounced antihypertensive effect can be detected at a dose of approximately 30 mg/kg p.o. and above.

Accordingly, the compounds of formula I and their salts can be used according to the invention in the prophylaxis and, especially, in the treatment of symptoms that can be influenced or caused by angiotensin II.

The compounds according to the invention can also be used for the treatment of glaucoma or for the reduction of ocular hypertension and for the promotion of retinal blood flow. Other possible uses for the angiotensin II-antagonists of formula I and their salts are in the treatment of secondary hyperaldosteronism, diabetic neuropathy or diabetic retinopathy, acute or chronic kidney failure, stroke, elevated uric acid level, antiangiogenesis, myocardial ischaemia (angina), myocardial infarct, hypertrophy of the left ventricle, myocardial fibrosis, insufficiency of the aorta, Alzheimer's disease, perceptual dysfunction, learning difficulties, senile dementia, schizophrenic polydipsia, depression, gastrointestinal motility, gastric secretion and intestinal absorption and for the prophylaxis and treatment of restenosis after percutaneous transluminal coronary angioplasty (PTCA).

The compounds I and their pharmaceutically acceptable salts can accordingly be used, for example, as active ingredients in antihypertensives which are used, for example, for the treatment of high blood pressure and cardiac insufficiency, and also for the treatment of glaucoma or for the reduction of ocular hypertension and for the promotion of retinal blood flow. The invention thus relates also to the use of the compounds I and their pharmaceutically acceptable salts for the preparation of corresponding medicaments and for the therapeutic treatment of disorders that are caused or influenced by angiotensin II, especially high blood pressure and cardiac insufficiency and also for the treatment of glaucoma or for the reduction of ocular hypertension and for the promotion of retinal blood flow. Preparation of the medicaments also includes commercial production of the active ingredients.

Preferred are compounds of formula I wherein $R_1$ is $C_1$–$C_7$alkyl that is unsubstituted or substituted by halogen or by hydroxy, or is $C_2$–$C_7$alkenyl, $C_3$–$C_7$cycloalkyl or $C_1$–$C_7$alkoxy; and their salts.

Preferred are compounds of formula I wherein $R_1$ is $C_2$–$C_7$alkyl or is $C_1$–$C_7$alkyl that is substituted by halogen or by hydroxy, or is $C_3$–$C_7$alkenyl, $C_3$–$C_6$cycloalkyl or $C_1$–$C_7$alkoxy;

$R_2$ is 1H-tetrazol-5-yl, carboxy, $C_1$–$C_4$alkoxycarbonyl or halo-$C_1$–$C_4$alkanesulfonylamino;

$R_3$ is 1H-tetrazol-5-yl, carboxy, $C_1$–$C_4$alkoxycarbonyl, $C_1$–$C_4$alkoxy-$C_1$–$C_4$alkoxycarbonyl, phenyl-$C_1$–$C_4$alkoxycarbonyl or carbamoyl, the amino group of which is mono-substituted by $C_1$–$C_4$alkyl or di-substituted by $C_1$–$C_4$alkyl groups which may be the same or different, or is di-substituted by $C_4$–$C_6$alkylene or by ethyleneoxyethylene;

Alk is methylene, ethylene or ethylidene;

Het is

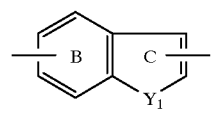

(i)

wherein $Y_1$ is O, S or N(R) and R is hydrogen or $C_1$–$C_4$alkyl; or

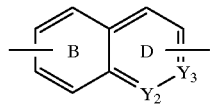

wherein one of the variables $Y_2$ and $Y_3$ is CH and the other is N or each of the variables is CH;

$X_1$ is —CO— or —S(O)$_m$— and the index m is 0, 1 or 2;

one of the variables $X_2$ and $X_4$ is $C_1$–$C_4$alkylene and the other of the variables $X_2$ and $X_4$ is a bond; or each of the variables $X_2$ and $X_4$ is a bond;

$X_3$ is $C_3$–$C_6$cycloalkylidene or the structural element —C($X_a$)($X_b$)— and $X_a$ is hydrogen or $C_1$–$C_7$alkyl and $X_b$ is $C_1$–$C_7$alkyl;

and the rings A, B, C and D, with the exception of the substituents indicated in the formula, and also aromatic substituents are, independently of one another, unsubstituted or mono- or poly-substituted by substituents selected from the group consisting of halogen, $C_1$–$C_4$alkyl, $C_1$–$C_4$alkoxy, $C_3$–$C_5$alkenyloxy, phenoxy, benzyloxy, trifluoromethyl and S(O)$_m$—R, wherein m is 0, 1 or 2 and R is hydrogen or $C_1$–$C_4$alkyl;

and their salts.

Preferred are compounds of formula I wherein $R_1$ is $C_2$–$C_7$alkyl or is $C_1$–$C_4$alkyl that is substituted by halogen or by hydroxy, or is $C_3$–$C_7$alkenyl, $C_3$–$C_6$cycloalkyl or $C_1$–$C_7$alkoxy;

$R_2$ is 1H-tetrazol-5-yl, carboxy or $C_1$–$C_4$alkoxycarbonyl;

$R_3$ is 1H-tetrazol-5-yl, carboxy, $C_1$–$C_4$alkoxycarbonyl, $C_1$–$C_4$alkoxy-$C_1$–$C_4$alkoxycarbonyl or phenyl-$C_1$–$C_2$alkoxycarbonyl;

Alk is methylene, also ethylene or ethylidene;

Het is

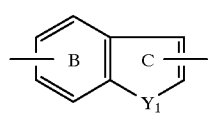

wherein $Y_1$ is O, S, or NH; or

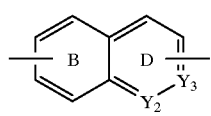

wherein one of the variables $Y_2$ and $Y_3$ is CH and the other is N or each of the variables is CH; especially

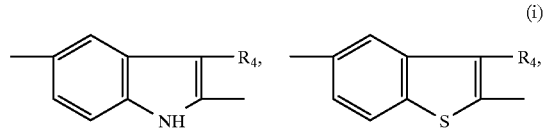

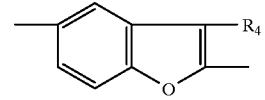

and $R_4$ is hydrogen, halogen, such as bromine, and also $C_1$–$C_7$alkyl, $C_1$–$C_7$alkoxy or trifluoromethyl; or

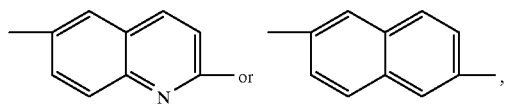

$X_1$ is —CO—;

one of the variables $X_2$ and $X_4$ is $C_1$–$C_2$alkylene and the other of the variables $X_2$ and $X_4$ is a bond; or each of the variables $X_2$ and $X_4$ is a bond;

$X_3$ is $C_5$–$C_6$cycloalkylidene or the structural element —C($X_a$)($X_b$)— and $X_a$ is hydrogen or $C_1$–$C_5$alkyl and $X_b$ is $C_1$–$C_5$alkyl; especially (i) $X_2$ is $C_1$–$C_2$alkylene; $X_4$ is a bond; $X_3$ is $C_5$–$C_6$cycloalkylidene; or (ii) each of the $X_2$ and $X_4$ is a bond; and $X_3$ is the structural element —C($X_a$)($X_b$)— and $X_a$ is hydrogen or $C_1$–$C_5$alkyl and $X_b$ is $C_1$–$C_5$alkyl;

and the rings A, B, C and D, with the exception of the substituents indicated in the formula, are, independently of one another, unsubstituted or mono- or poly-substituted by substituents selected from the group consisting of halogen, $C_1$–$C_4$alkyl, $C_1$–$C_4$alkoxy and trifluoromethyl; and their salts.

Preferred are compounds of the formula of the type defined above in each case wherein one of the variables $Y_2$ and $Y_3$ is C(R') and the other is N or C(R'), wherein R' is halogen, $C_1$–$C_4$alkyl, $C_1$–$C_4$alkoxy or trifluoromethyl, and their salts.

Preferred are compounds of formula I wherein $R_1$ is $C_2$–$C_7$alkyl, such as n-propyl or n-butyl, or $C_3$–$C_6$cycloalkyl, such as cyclopropyl, or $C_1$–$C_4$alkoxy, such as methoxy, ethoxy, propoxy or butoxy;

$R_2$ is 1H-tetrazol-5-yl, carboxy or $C_1$–$C_4$alkoxycarbonyl, such as methoxy- or ethoxycarbonyl;

$R_3$ is carboxy or $C_1$–$C_4$alkoxycarbonyl, such as methoxy-, ethoxy- or tert-butoxy-carbonyl;

Alk is methylene;

Het is

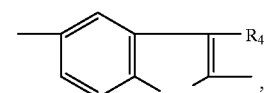

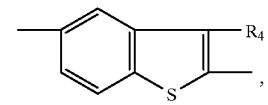

-continued

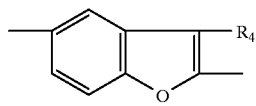

and $R_4$ is hydrogen, halogen, such as bromine, also $C_1$–$C_4$alkyl, such as methyl, $C_1$–$C_4$alkoxy, such as methoxy, or trifluoromethyl; or

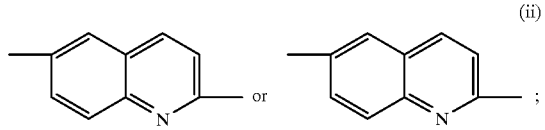

(ii)

$X_1$ is —CO—;

(i) $X_2$ is $C_1$–$C_2$alkylene, especially methylene; $X_4$ is a bond; $X_3$ is $C_5$–$C_6$cycloalkylidene; or (ii) each of $X_2$ and $X_4$ is a bond; and $X_3$ is the structural element —C($X_a$)($X_b$)— and $X_a$ is hydrogen or $C_1$–$C_5$alkyl, such as ethyl, and $X_b$ is $C_1$–$C_5$alkyl, such as ethyl or isopropyl; and their salts.

Preferred are compounds of the formula, and their salts, of the type defined above in each case wherein $R_3$ is hydroxymethyl, $C_1$–$C_4$alkoxymethyl or formyl; the other variables are as defined above in each case.

Preferred are compounds of formula I wherein $R_1$ is $C_2$–$C_5$alkyl, such as n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

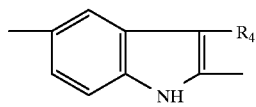

and $R_4$ is hydrogen, halogen, such as bromine, or $C_1$–$C_4$alkyl, such as methyl;

$X_1$ is —CO—;

(i) $X_2$ is $C_1$–$C_2$alkylene, especially methylene; $X_4$ is a bond; $X_3$ is $C_5$–$C_6$cycloalkylidene; or (ii) each of $X_2$ and $X_4$ is a bond; and $X_3$ is the structural element —C($X_a$)($X_b$)— and $X_a$ is hydrogen or $C_1$–$C_5$alkyl, such as ethyl, and $X_b$ is $C_1$–$C_5$alkyl, such as ethyl, isopropyl or 3-butyl; and their salts.

Preferred are compounds of formula I wherein $R_1$ is $C_2$–$C_5$alkyl, such as n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

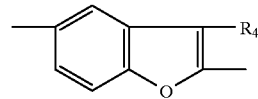

and $R_4$ is hydrogen, halogen, such as bromine, or $C_1$–$C_4$alkyl, such as methyl;

$X_1$ is —CO—;

(i) $X_2$ is $C_1$–$C_2$alkylene, especially methylene; $X_4$ is a bond; $X_3$ is a $C_5$–$C_6$cycloalkylidene; or (ii) each of $X_2$ and $X_4$ is a bond; and $X_3$ is the structural element —C($X_a$)($X_b$)— and $X_a$ is hydrogen or $C_1$–$C_5$alkyl, such as ethyl, and $X_b$ is $C_1$–$C_5$alkyl, such as ethyl, isopropyl or 3-butyl; and their salts.

Preferred are compounds of formula I wherein $R_1$ is $C_2$–$C_5$alkyl, such as n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

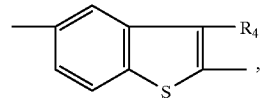

wherein $R_4$ is hydrogen, halogen, such as bromine, or $C_1$–$C_4$alkyl, such as methyl;

$X_1$ is —CO—;

(i) $X_2$ is $C_1$–$C_2$alkylene, especially methylene; $X_4$ is a bond; $X_3$ is $C_5$–$C_6$cycloalkylidene, such as cyclopentylidene or cyclohexylidene; or (ii) each of $X_2$ and $X_4$ is a bond; and $X_3$ is the structural element —C($X_a$)($X_b$)— and $X_a$ is hydrogen or $C_1$–$C_5$alkyl, such as ethyl, and $X_b$ is $C_1$–$C_5$alkyl, such as ethyl, isopropyl or 3-butyl; and their salts.

Preferred are compounds of formula I wherein $R_1$ is $C_2$–$C_5$alkyl, such as n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

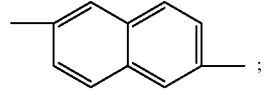

$X_1$ is —CO—;

(i) $X_2$ is $C_1$–$C_2$alkylene, especially methylene; $X_4$ is a bond; $X_3$ is $C_5$–$C_6$cycloalkylidene; or (ii) each of $X_2$ and $X_4$ is a bond; and $X_3$ is the structural element —C($X_a$)($X_b$)— and $X_a$ is hydrogen or $C_1$–$C_5$alkyl, such as ethyl, and $X_b$ is $C_1$–$C_5$alkyl, such as ethyl, isopropyl or 3-butyl; and their salts.

Preferred are compounds of formula I wherein $R_1$ is $C_2$–$C_5$alkyl, such as n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

[structure: 6-methylquinolin-2-yl]

$X_1$ is —CO—;

(i) $X_2$ is $C_1$–$C_2$alkylene, especially methylene; $X_4$ is a bond; $X_3$ is $C_5$–$C_6$cycloalkylidene; or (ii) each of $X_2$ and $X_4$ is a bond; and $X_3$ is the structural element —$C(X_a)(X_b)$— and $X_a$ is hydrogen or $C_1$–$C_5$alkyl, such as ethyl, and $X_b$ is $C_1$–$C_5$alkyl, such as ethyl, isopropyl or 3-butyl; and their salts.

Preferred are compounds of formula I wherein $R_1$ is $C_2$–$C_5$alkyl, such as ethyl, n-propyl or n-butyl;

$R_2$ is 1H-tetrazol-5-yl or carboxy;

$R_3$ is carboxy or $C_1$–$C_4$alkoxycarbonyl, such as methoxy-, ethoxy- or tert-butoxy-carbonyl;

Alk is methylene;

Het is

[structure: benzofuran with $R_4$ substituent]

and $R_4$ is hydrogen or halogen having an atomic number of up to and including 35, such as bromine;

$X_1$ is —CO—;

(i) $X_2$ is $C_1$–$C_2$alkylene, especially methylene; $X_4$ is a bond; $X_3$ is $C_5$–$C_6$cycloalkylidene; or (ii) each of $X_2$ and $X_4$ is a bond; and $X_3$ is the structural element —$C(X_a)(X_b)$— and $X_a$ is hydrogen or $C_1$–$C_5$alkyl, such as ethyl, and $X_b$ is $C_1$–$C_5$alkyl, such as ethyl, isopropyl or 3-butyl; and their salts.

Especially preferred are the compounds of formula I mentioned in the Examples, in free form or in salt form.

The invention relates also to a process for the preparation of the compounds I and their salts, wherein, for example.

a) in a compound of the formula $$R_1-X_1-N(X_2-X_3-X_4-R_3)-Alk-Het-A-Z_1 \quad (II)$$

or in a salt thereof, wherein $Z_1$ is a radical that can be converted into $R_2$, $Z_1$ is converted into $R_2$; or b) a compound of the formula $$HN(X_2-X_3-X_4-R_3)-Alk-Het-A-R_2 \quad (IIIa)$$

is reacted with a compound of the formula $R_1$—$X_1$—OH (IIIb), a reactive derivative thereof or a salt thereof;

and, in each case, if desired, a compound I obtainable according to the process or by another method, in free form or in salt form, is isolated, a compound I obtainable according to the process or by another method is converted into a different compound I, a mixture of isomers obtainable according to the process is separated and the desired isomer is isolated and/or a free compound I obtainable according to the process is converted into a salt, or a salt, obtainable according to the process, of a compound I is converted into the free compound I or into a different salt.

Salts of starting materials having at least one basic centre are corresponding acid addition salts, while salts of starting materials having at least one acidic group are salts with bases, in each case as indicated hereinbefore in connection with corresponding salts of compounds I.

Radicals $Z_1$ that can be converted into the variable $R_2$ are, for example, cyano, mercapto, halogen, the group —$N_2^+A^-$, in which $A^-$ is an anion derived from an acid, such as a halide, amino and also functionally modified forms other than COOH, $SO_3H$, $PO_3H_2$ and $PO_2H_2$, and also N-protected 1H-tetrazol-5-yl.

Reactive derivatives of compounds of formula IIIb are, for example, activated esters or reactive anhydrides, or also reactive cyclic amides, each derived therefrom.

The reactions described hereinbefore and hereinafter in the variants are carried out in a manner known per se, for example in the absence or, generally, in the presence of a suitable solvent or diluent or a mixture thereof, the reactions being carried out, as required, with cooling, at room temperature or with heating, for example in a temperature range of from approximately −80° C. up to the boiling temperature of the reaction medium, preferably from approximately −10° to approximately +200° C., and, if necessary, in a closed vessel, under pressure, in an inert gas atmosphere and/or under anhydrous conditions. Details of corresponding procedures and reaction conditions can be found especially also in the Examples.

Process variant a):

Radicals $Z_1$ that can be converted into 1H-tetrazol-5-yl $R_2$ are, for example, cyano or protected 1H-tetrazol-5-yl.

For the preparation of compounds of formula I wherein $R_2$ is 1H-tetrazol-5-yl, for example starting material of formula II wherein $Z_1$ is cyano is used, and this starting material is reacted with azide, such as $HN_3$ or especially a salt, such as an alkali metal salt, thereof or with the ammonium azide or an organotin azide, such as tri-(lower) alkylammonium azide and tri-(lower) alkyl- or triaryl-tin azide. Preferred azides are, for example, sodium and potassium azide and also tri-$C_1$–$C_4$alkylammonium azide, tri-$C_1$–$C_4$alkyltin azide and triaryltin azide, for example triethylammonium azide, triethyl tributyl-tin azide, and triphenyltin azide. Some of the azides can be formed in situ in a manner known per se. The formation of tetrazol-5-yl is preferably carried out with compounds of formula II wherein $R_2$ is other than carboxy.

Suitable protecting groups of protected 1H-tetrazol-5-yl are the protecting groups customarily used in tetrazole chemistry, especially triphenylmethyl, unsubstituted or substituted, for example nitro-substituted, benzyl, such as 4-nitrobenzyl, lower alkoxymethyl, such as methoxy- and ethoxy-methyl, also 1-ethoxyethyl, lower alkylthiomethyl, such as methylthiomethyl, silyl, such as tri-lower alkylsilyl, for example dimethyl-tert-butyl- and triisopropyl-silyl, and also 2-cyanoethyl, also lower alkoxy-lower alkoxymethyl, such as 2-methoxyethoxymethyl, benzyloxymethyl and phenacyl.

The removal of the protecting groups is carried out in accordance with known methods, for example as described in J. Green, Protective Groups in Organic Synthesis, Wiley-Interscience (1980). For example, the triphenylmethyl group is customarily removed by hydrolysis, especially in the presence of an acid, or by hydrogenolysis in the presence of a hydrogenation catalyst, 4-nitrobenzyl is removed, for example, by hydrogenolysis in the presence of a hydrogenation catalyst, methoxy- or ethoxy-methyl is removed, for example, by treatment with a tri-lower alkyl-, such as triethyl- or tributyl-tin bromide, methylthio-methyl is removed, for example, by treatment with trifluoroacetic acid, silyl radicals are removed, for example, by treatment with fluorides, such as tetra-lower alkylammonium fluorides, for example tetrabutylammonium fluoride, or alkali metal fluorides, for example sodium fluoride, 2-cyanoethyl is removed, for example, by hydrolysis, for example with sodium hydroxide solution, 2-methoxyethoxymethyl is removed, for example, by hydrolysis, for example with hydrochloric acid, and benzyloxymethyl and phenacyl are removed, for example, by hydrogenolysis in the presence of a hydrogenation catalyst.

A radical that can be converted into $R_2=SO_3H$ is, for example, the mercapto group. Starting compounds of formula II having such a group are oxidised, for example, by oxidation processes known per se to form compounds of formula I wherein $R_2$ is $SO_3H$. Suitable oxidising agents are, for example, inorganic per-acids, such as per-acids of mineral acids, for example periodic acid or persulfuric acid, organic per-acids, such as corresponding percarboxylic or persulfonic acids, for example performic, peracetic, trifluoroperacetic or perbenzoic acid or p-toluenepersulfonic acid, or mixtures of hydrogen peroxide and acids, for example a mixture of hydrogen peroxide and acetic acid.

The oxidation is often carried out in the presence of suitable catalysts, and there may be mentioned as catalysts suitable acids, such as unsubstituted or substituted carboxylic acids, for example acetic acid or trifluoroacetic acid, or transition metal oxides, such as oxides or elements of sub-group VII, for example vanadium, molybdenum or tungsten oxide. The oxidation is carried out under mild conditions, for example at temperatures of from approximately −50° to approximately +100° C.

A group that can be converted into $R_2=PO_3H_2$ is to be understood as being, for example, a group $N_2^+A^-$, wherein $A^-$ is an anion of an acid, such as a mineral acid. Such diazonium compounds are reacted, for example, in a manner known per se with a P(III) halide, such as $PCl_3$ or $PBr_3$, and are worked up by hydrolysis, compounds of formula I wherein $R_2$ is $PO_3H_2$ being obtainable.

A suitable radical $Z_1$ that can be converted into halo-$C_1$–$C_7$alkanesulfonylamino $R_2$ is, for example, primary amino.

For the preparation of compounds of formula I wherein $R_2$ is halo-$C_1$–$C_7$alkanesulfonylamino, for example corresponding anilines are reacted with a customarily reactively derivatised, for example esterified, halo-$C_1$–$C_7$alkanesulfonic acid, the reaction, if desired, being carried out in the presence of a base. Suitable as the preferred reactively esterified halosulfonic acid is the corresponding halide, such as chloride or bromide.

A radical $Z_1$ that can be converted into $R_2=COOH$ is, for example, functionally modified carboxy, such as cyano, esterified or amidated carboxy, hydroxymethyl or formyl.

Esterified carboxy is, for example, carboxy esterified by an unsubstituted or substituted aliphatic, cycloaliphatic or aromatic alcohol. An aliphatic alcohol is, for example, a lower alkanol, such as methanol, ethanol, propanol, isopropanol, n-butanol, sec- or tert-butanol, while a suitable cycloaliphatic alcohol is, for example, a 3- to 8-membered cycloalkanol, such as cyclo-pentanol, -hexanol or -heptanol. An aromatic alcohol is, for example, a phenol or heterocyclic alcohol, each of which may be unsubstituted or substituted, especially hydroxypyridine, for example 2-, 3- or 4-hydroxypyridine. Carboxy may also be esterified by a silylated alcohol and is especially tri-($C_1$–$C_4$)alkylsilyl-($C_1$–$C_4$)alkoxycarbonyl, especially trimethylsilylethoxycarbonyl.

Amidated carboxy is, for example, carbamoyl, or carbamoyl mono-substituted by hydroxy, amino or by unsubstituted or substituted phenyl, carbamoyl mono- or di-substituted by lower alkyl, or carbamoyl di-substituted by 4- to 7-membered alkylene, or by 3-aza, 3-lower alkylaza, 3-oxo- or 3-thia-alkylene. There may be mentioned as examples: carbamoyl, N-mono- or N,N-di-lower alkylcarbamoyl, such as N-methyl-, N-ethyl-, N,N-dimethyl-, N,N-diethyl- or N,N-dipropyl-carbamoyl, pyrrolidino- or piperidino-carbonyl, morpholino-, piperazino- and 4-methylpiperazino- or thiomorpholino-carbonyl, anilinocarbonyl or anilinocarbonyl substituted by lower alkyl, lower alkoxy and/or by halogen.

Preferred functionally modified carboxy is, for example, tri-($C_1$–$C_4$)alkylsilyl-($C_1$–$C_4$)alkoxycarbonyl, especially trimethylsilylethoxycarbonyl, or cyano. Compounds of formula I wherein $R_2$ is carboxy can be prepared, for example, starting from compounds of formula II wherein $Z_1$ is functionally modified carboxy, in a manner known per se, for example by hydrolysis, especially in the presence of a base, in the case of corresponding tri-($C_1$–$C_4$)alkylsilyl-($C_1$–$C_4$) alkoxycarbonyl derivatives, for example, by treatment with an ammonium fluoride, such as a tetra-lower alkylammonium fluoride, for example tetra-n-butylammonium fluoride, or, in the case of benzyloxycarbonyl derivatives, by hydrogenolysis in the presence of a hydrogenation catalyst, or starting from compounds of formula II wherein $Z_1$ is hydroxymethyl or formyl, by oxidation using customary oxidising agents.

The oxidation is carried out, for example, in an inert solvent, such as a lower alkane-carboxylic acid, for example acetic acid, a ketone, for example acetone, an ether, for example tetrahydrofuran, a heterocyclic aromatic compound, for example pyridine, or water or a mixture thereof, if necessary with cooling or heating, for example at from approximately 0° to approximately 150° C. Suitable oxidising agents are, for example, oxidising transition metal compounds, especially those with elements of sub-group, I, VI or VIII. There may be mentioned as examples: silver compounds, such as silver nitrate, oxide or picolinate, chromium compounds, such as chromium trioxide or potassium dichromate, manganese compounds, such as potassium permanganate, tetrabutylammonium permanganate or benzyl(triethyl)ammonium permanganate. Other oxidising agents are, for example, suitable compounds with elements of main group IV, such as lead dioxide, or halogen-oxygen compounds, such as sodium periodate or potassium periodate.

For example, hydroxymethyl and formyl are oxidised to form carboxy $R_2$.

This variant is preferably suitable for the preparation of compounds of formula I in which the variables have meanings other than unsaturated radicals.

Suitable bases are, for example, alkali metal hydroxides, hydrides, amides, alkanolates, carbonates, triphenylmethylides, di-lower alkylamides, aminoalkylamides and lower alkylsilylamides; also naphthaleneamines, lower alkylamines, basic heterocycles, ammonium hydroxides, and carbocyclic amines. There may be mentioned by way of example: sodium hydroxide, hydride and amide, sodium methanolate and ethanolate, potassium tert-butanolate and carbonate, lithium triphenylmethylide and diisopropylamide, potassium 3-(aminopropyl)-amide and bis(trimethylsilyl)amide, dimethylaminonaphthalene, di- or tri-ethylamine, or ethyldiisopropylamine, N-methylpiperidine, pyridine, benzyltrimethylammonium hydroxide, 1,5-diazabicyclo[4.3.0]non-5-ene (DBN) and 1,8-diazabicyclo[5.4.0]undec-7-ene (DBU).

The starting material of formula II can be prepared in a manner known per se.

For example, the starting material of formula II can be obtained by reacting a compound of the formula

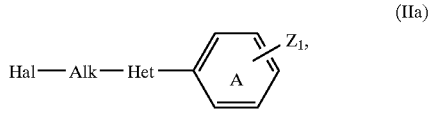
(IIa)

wherein Hal is, for example, halogen, with a compound of the formula $H_2N-X_2-X_3-X_4-R_3$ (IIb) or with a salt thereof, if necessary in the presence of a base, and reacting a compound so obtainable of the formula

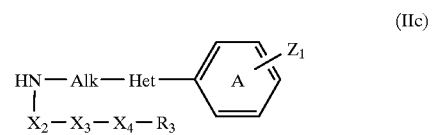
(IIc)

with a compound of the formula $R_1-X_1-OH$ (IIIb), a reactive derivative thereof or a salt thereof, if necessary in the presence of a base.

The compounds of formula IIa are prepared in a manner known per se. Further details can be found in the Examples. Process variant b):

Activated esters of compounds of formula IIIb are especially esters that are unsaturated at the linking carbon atom of the esterifying radical, for example esters of the vinyl ester type, such as vinyl esters (obtainable, for example, by transesterification of a corresponding ester with vinyl acetate; activated vinyl ester method), carbamoyl vinyl esters (obtainable, for example, by treating the corresponding acid with an isoxazolium reagent; 1,2-oxazolium or Woodward method) or 1-lower alkoxyvinyl esters (obtainable, for example, by treating the corresponding acid with a lower alkoxyacetylene; ethoxyacetylene method), or esters of the amidino type, such as N,N'-di-substituted amidino esters (obtainable, for example, by treating the corresponding acid with a suitable N,N'-di-substituted carbodiimide, for example N,N'-dicyclohexylcarbodiimide; carbodiimide method) or N,N-di-substituted amidino esters (obtained, for example, by treating the corresponding acid with an N,N-di-substituted cyanamide; cyanamide method), suitable aryl esters, especially phenyl esters substituted by electron-attracting substituents (obtainable, for example, by treating the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treating the corresponding acid with chloroacetonitrile in the presence of a base; cyanomethyl esters method), thio esters, especially unsubstituted or substituted, for example nitro-substituted, phenylthio esters (obtainable, for example, by treating the corresponding acid with unsubstituted or substituted, for example nitro-substituted, thiophenols, using, inter alia, the anhydride or carbodiimide method; activated thiol esters method) or especially amino or amido esters (obtainable, for example, by treating the corresponding acid with an N-hydroxyamino or N-hydroxyamido compound, respectively, and the activated derivatives thereof, for example N-hydroxysuccinimide, N-hydroxypiperidine, N-hydroxyphthalimide, N-hydroxy-5-norbornene or -norbornane-2,3-dicarboxylic acid imide, 1-hydroxybenzotriazole or benzotriazol-1-yloxyphosphonium salts or benzotriazol-1-yluronium salts, or 3-hydroxy-3,4-dihydro-1,2,3-benzotriazin-4-one, for example in accordance with the anhydride or carbodiimide method; activated N-hydroxy esters method).

Anhydrides of acids may be symmetric or, preferably, mixed anhydrides of those acids, for example anhydrides with inorganic acids, such as acid halides, especially acid chlorides (obtainable, for example, by treating the corresponding acid with thionyl chloride, phosphorus pentachloride or oxalyl chloride; acid chloride method), azides (obtainable, for example, from a corresponding acid ester by way of the corresponding hydrazide and treatment thereof with nitrous acid; azide method), anhydrides with carbonic acid semi-esters, for example carbonic acid lower alkyl semi-esters (obtainable, for example, by treating the corresponding acid with chloroformic acid lower alkyl esters or with a 1-lower alkoxycarbonyl-2-lower alkoxy-1,2-dihydroquinoline, for example 1-ethoxycarbonyl-2-ethoxy-1,2-dihydroquinoline; mixed O-alkylcarbonic acid anhydrides method), anhydrides with dihalogenated, especially dichlorinated, phosphoric acid (obtainable, for example, by treating the corresponding acid with phosphorus oxychloride; phosphorus oxychloride method), anhydrides with ether phosphoric acid derivatives (for example those which can be obtained with phenyl-N-phenylphosphoramidochloridate) or with phosphorous acid derivatives, or anhydrides with organic acids, such as mixed anhydrides with organic carboxylic acids (obtainable, for example, by treating the corresponding acid with an unsubstituted or substituted lower alkane- or phenyl-lower alkane-carboxylic acid halide, for example phenylacetic acid, pivalic acid or trifluoroacetic acid chloride; mixed carboxylic acid anhydrides method) or with organic sulfonic acids (obtainable, for example, by treating a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method), and also symmetric anhydrides (obtainable, for example, by condensing the corresponding acid in the presence of a carbodiimide or 1-diethylaminopropyne; symmetric anhydrides method).

Suitable cyclic amides are especially amides having five-membered diazacycles of aromatic nature, such as amides with imidazoles, for example imidazole (obtainable, for example, by treating the corresponding acid with N,N'- carbonyldiimidazole; imidazole method), or pyrazoles, for example 3,5-dimethylpyrazole (obtainable, for example, by way of the acid hydrazide by treatment with acetylacetone; pyrazolide method).

The condensation for the production of the amide bond can be carried out in a manner known per se, for example as described in standard works, such as "Houben-Weyl, Methoden der organischen Chemie", 4th edition, Volume 15/II, Georg Thieme Verlag, Stuttgart 1974, "The Peptide" (Editors E. Gross and J. Meienhofer), Volumes 1 and 2, Academic Press, London and New York, 1979/1980, or M. Bodanszky, "Principles of Peptide Synthesis", Springer-Verlag, Berlin 1984.

The condensation can be carried out in the presence of one of the customary condensation agents. Customary condensation agents are, for example, carbodiimides, for example diethyl-, dipropyl-, N-ethyl-N'-(3-dimethylaminopropyl)-carbodiimide or, especially, dicyclohexylcarbodiimide, also suitable carbonyl compounds, for example carbonyldiimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, also activated phosphoric acid derivatives, for example diphenylphosphorylazide, diethylphosphoryl cyanide, phenyl-N-phenylphosphoramidochloridate, bis(2-oxo-3-oxazolidinyl)phosphinic acid chloride or 1-benzotriazolyloxy-tri(dimethylamino)phosphonium hexafluorophosphate.

If desired, an organic base is added, for example a tri-lower alkylamine having voluminous radicals, for example ethyldiisopropylamine, or a heterocyclic base, for example pyridine, 4-dimethylaminopyridine or, preferably, N-methymorpholine.

The condensation of acid anhydrides with amines can be carried out, for example, in the presence of inorganic carbonates, for example alkali metal carbonates or alkali metal hydrogen carbonates, such as sodium or potassium carbonate or hydrogen carbonate (customarily together with a sulfate).

The condensation is preferably carried out in an inert polar aprotic, preferably non-aqueous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, cyclic ethers, for example tetrahydrofuran, an ester, for example ethyl acetate, or a nitrile, for example acetonitrile, or in mixtures thereof, where appropriate at reduced or elevated temperature, for example in a temperature range of from approximately −40° C. to approximately +100° C., preferably from approximately −10° C. to approximately +50° C., and, if desired, under an inert gas atmosphere, for example a nitrogen atmosphere.

Reactive acid derivatives can also be formed in situ.

The starting material of formulae IIIa and IIIb is known or can be prepared in a manner known per se.

For example, the starting material of formula IIIa can be obtained by converting $Z_1$ in a compound of the formula

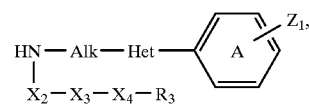

into $R_2$ in the manner indicated in variant a).

More detailed information on the processes for the preparation of corresponding starting compounds or their precursors can be found in the Examples.

A compound I obtainable according to the process or by another method can be converted in a manner known per se into a different compound I.

A compound according to the invention containing hydroxy can be etherified according to methods known per se. The etherification can be carried out, for example, with an alcohol, such as an unsubstituted or substituted $C_1$–$C_7$alkanol, or a reactive ester of the same. Suitable reactive esters of the desired alcohols are, for example, those with strong inorganic or organic acids, such as corresponding halides, sulfates, lower alkanesulfonates or unsubstituted or substituted benzenesulfonates, for example chlorides, bromides, iodides, methane-, benzene- or p-toluene-sulfonates. The etherification can be carried out, for example, in the presence of a base, an alkali metal hydride, hydroxide or carbonate or an amine. Conversely, corresponding ethers, such as $C_1$–$C_7$alkoxy compounds, can be cleaved, for example, by means of strong acids, such as mineral acids, for example the hydrohalic acids hydrobromic or hydriodic acid, which may advantageously be in the form of pyridinium halides, or by means of Lewis acids, for example halides of elements of main group III or of the corresponding sub-groups. Those reactions can, if necessary, be carried out with cooling or heating, for example in a temperature range of from approximately −20° to approximately 100° C., in the presence or absence of a solvent or diluent, under an inert gas and/or under pressure and, if desired, in a closed vessel.

Compounds according to the invention containing hydroxymethyl groups can be prepared, for example, starting from corresponding compounds containing carboxy or esterified carboxy, corresponding compounds being reduced in a manner known per se, for example by reduction with an optionally complex hydride, such as a hydride formed from an element of main groups I and III of the Periodic Table of Elements, for example boranate or alanate, for example lithium borohydride, lithium hydride and diisobutylaluminium hydride (a subsequent reduction step using an alkali metal cyanoborohydride, such as sodium cyanoborohydride, may be necessary), and also diborane.

If a structural constituent is substituted by ($C_1$–$C_7$) alkythio (in $S(O)_m$—R, m is 0), the latter can be converted in customary manner into corresponding ($C_1$–$C_7$)alkane-sulfinyl or -sulfonyl. Suitable oxidising agents for the oxidation to the sulfoxide stage are, for example, inorganic per-acids, such as per-acids of mineral acids, for example periodic acid or persulfuric acid, organic per-acids, such as corresponding percarboxylic or persulfonic acids, for example performic, peracetic, trifluoroperacetic or perbenzoic acid or p-toluene-persulfonic acid, or mixtures of hydrogen peroxide and acids, for example a mixture of hydrogen peroxide and acetic acid.

The oxidation is often carried out in the presence of suitable catalysts, and there may be mentioned as catalysts suitable acids, such as unsubstituted or substituted carboxylic acids, for example acetic acid or trifluoroacetic acid, or transition metal oxides, such as oxides of elements of sub-group VII, for example vanadium, molybdenum or tungsten oxide. The oxidation is carried out under mild conditions, for example at temperatures of from approximately −50° to approximately +100° C.

The oxidation to the sulfone stage can also be carried out in corresponding manner with dinitrogen tetroxide as catalyst in the presence of oxygen at low temperatures, as can the direct oxidation of the (lower) alkylthio to the (lower) alkanesulfonyl. In this case, however, the oxidising agent is normally used in excess.

If one of the variables contains amino, corresponding compounds of formula I, their tautomers or salts can be N-alkylated in a manner known per se. The (phenyl-)$C_1$–$C_7$alkylation is carried out, for example, with a reactive ester of a (phenyl-)$C_1$–$C_7$alkyl halide, for example bromide or iodide, a (phenyl-)$C_1$–$C_7$alkylsulfonate, for example methanesulfonate or p-toluenesulfonate, or a di-$C_1$–$C_7$alkyl sulfate, for example dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, although more strongly basic condensation agents, such as alkali metal amides, hydrides or alcoholates, for example sodium amide, sodium hydride or sodium ethanolate, may be necessary. Likewise, amino can be acylated in a manner known per se, for example analogously to variant b).

In compounds of formula I that contain an esterified or amidated carboxy group as substituent, such a group can be converted into a free carboxy group, for example by means of hydrolysis, for example in the presence of a basic agent, or an acidic agent, such as a mineral acid. For example, tert-butoxycarbonyl can also be converted into carboxy, for example, in a manner known per se, such as by treatment with trihaloacetic acid, such as trifluoroacetic acid, and benzyloxycarbonyl can be converted into carboxy, for example, by catalytic hydrogenation in the presence of a hydrogenation catalyst, for example in the manner described hereinafter.

Furthermore, in compounds of formula I that contain a carboxy group as substituent, especially if $R_3$ is other than carboxy, the carboxy group can be converted into an esterified carboxy group, for example by treatment with an alcohol, such as a $C_1$–$C_7$alkanol, in the presence of a suitable esterification agent, such as an acidic reagent, for example an inorganic or organic acid or a Lewis acid, for example zinc chloride, or a condensation agent that binds the elements of water, for example a carbodiimide, such as N,N'-dicyclohexylcarbodiimide, or by treatment with a diazo reagent, such as with a diazo-lower alkane, for example diazomethane. An esterified carboxy group can also be obtained if compounds of formula I in which the carboxy group is in free form or in the form of a salt, such as an ammonium or metal salt, for example an alkali metal salt, such as a sodium or potassium salt, is treated with a reactive ester of a ($C_1$–$C_7$)alkyl halide, for example methyl or ethyl bromide or iodide, or with an organic sulfonic acid ester, such as a corresponding ($C_1$–$C_7$)alkyl ester, for example methanesulfonic acid or p-toluenesulfonic acid methyl ester or ethyl ester.

Compounds of formula I that contain an esterified carboxy group as substituent can be converted into other ester compounds of formula I by transesterification, for example by treatment with an alcohol, customarily a higher alcohol than the alcohol corresponding to the esterified carboxy group in the starting material, in the presence of a suitable transesterification agent, such as a basic agent, for example an alkali metal ($C_1$–$C_7$)alkanoate, ($C_1$–$C_7$)alkanolate or cyanide, such as sodium acetate, methanolate, ethanolate, tert-butanolate or cyanide, or a suitable acidic agent, if desired with removal of the resulting alcohol, for example by distillation. It is also possible to start from corresponding so-called activated esters of formula I that contain an activated esterified carboxy group as substituent (see below) and to convert the latter into a different ester by treatment with, for example, a ($C_1$–$C_7$)alkanol.

In compounds of formula I that contain a carboxy group as substituent, the latter can also first be converted into a reactive derivative, such as an anhydride, including a mixed anhydride, such as an acid halide, for example chloride (for example by treatment with a thionyl halide, for example chloride), or an anhydride with a formic acid ester, for example formic acid ($C_1$–$C_7$)alkyl ester (for example by treatment of a salt, such as an ammonium or alkali metal salt, with a halo-, such as chloro-, formic acid ester, such as a ($C_1$–$C_7$)alkyl ester), or into an activated ester, such as cyanomethyl, nitrophenyl, for example 4-nitrophenyl, or polyhalophenyl, for example pentachlorophenyl, ester (for example by treatment with a corresponding hydroxy compound in the presence of a suitable condensation agent, such as N,N'-dicyclohexylcarbodiimide), and such a reactive derivative can then be reacted with an amine thus to obtain amide compounds of formula I that contain an amidated carboxy group as substituent. These can be obtained directly or by way of intermediates; for example, an activated ester, such as a 4-nitrophenyl ester, of a compound of formula I having a carboxy group can first be reacted with 1-unsubstituted imidazole and the resulting 1-imidazolylcarbonyl compound can be reacted with an amine. It is, however, also possible to react with amines other, non-activated esters, such as ($C_1$–$C_7$)alkyl esters of compounds of formula I that contain, for example, ($C_2$–$C_8$) alkoxycarbonyl as substituent.

Compounds of formula I wherein $R_2$ is carboxy can be prepared by oxidation in a manner known per se using customary oxidising agents, for example starting from compounds of formula I wherein $R_2$ is hydroxymethyl or formyl. The oxidation is carried out, for example, in an inert solvent, such as a $C_1$–$C_7$alkanecarboxylic acid, for example acetic acid, a ketone, for example acetone, an ether, for example tetrahydrofuran, a heterocyclic aromatic compound, for example pyridine, or water or a mixture thereof, if necessary with cooling or heating, for example at from approximately 0° to approximately 150° C. Suitable oxidising agents are, for example, oxidising transition metal compounds, especially those with elements of sub-groups I, VI or VIII. There may be mentioned as examples: silver compounds, such as silver nitrate, oxide or picolinate, chromium compounds, such as chromium trioxide or potassium dichromate, manganese compounds, such as potassium permanganate, tetrabutylammonium permanganate or benzyl(triethyl) ammonium permanganate. Other oxidising agents are, for example, suitable compounds with elements of main group IV, such as lead dioxide, or halogen-oxygen compounds, such as sodium periodate or potassium periodate.

If an aromatic ring contains a hydrogen atom as substituent, the hydrogen atom can be replaced by a halogen atom in the customary manner using a halogenation agent, for example it can be brominated using bromine, hypobromic acid, acylhypobromite or other organic bromine compounds, for example N-bromosuccinimide, N-bromoacetamide, N-bromophthalimide, pyridinium perbromide, dioxane dibromide, 1,3-dibromo-5,5-dimethylhydantoin or 2,4,4,6-tetrabromo-2,5-cyclohexanedien-1-one, or chlorinated using elemental chlorine, for example in a halogenated hydrocarbon, such as chloroform, and with cooling, for example to from approximately −10° to approximately +100° C.

If an aromatic ring in the compounds according to the invention contains an amino group, the latter can be diazotised in customary manner, for example by treatment with a nitrite, for example sodium nitrite, in the presence of a suitable protonic acid, for example a mineral acid, the reaction temperature advantageously being maintained below approximately 5° C. The diazonium group so obtainable, which is in salt form, can be substituted in accordance with analogous methods, for example as follows: by a hydroxy group analogously to phenolthermolysis in the presence of water; by an alkoxy group by treatment with a corresponding alcohol, it being necessary to supply energy; by a fluorine atom analogously to Schiemann's reaction in the thermolysis of corresponding diazonium tetrafluoroborates; by the halogen atoms chlorine, bromine or iodine and also the cyano group analogously to Sandmeyer's reaction in the reaction with corresponding Cu(I) salts, first with cooling, for example to approximately below 5° C., and then with heating, for example to from approximately 60° to approximately 150° C.

If the compounds of formula I contain unsaturated radicals, such as ($C_3$–$C_7$)alkenyl groupings, the latter can be converted in a manner known per se into saturated radicals. For example, the hydrogenation of multiple bonds is effected by catalytic hydrogenation in the presence of hydrogenation catalysts, there being suitable for the purpose, for example, nickel, such as Raney nickel, and noble metals or their derivatives, for example oxides, such as palladium, and platinum oxide, which may, if appropriate, be supported on carrier materials, for example carbon or calcium carbonate. The hydrogenation can preferably be carried out at pressures of from 1 to approximately 100 atmospheres and from approximately −80° to approximately 200° C., especially from room temperature to approximately 100° C. The reaction is advantageously carried out in a solvent, such as water, a lower alkanol, for example ethanol, isopropanol or n-butanol, an ether, for example dioxane, or a lower alkanecarboxylic acid, for example acetic acid.

The invention relates especially to the processes described in the Examples.

Salts of compounds I can be prepared in a manner known per se. For example, acid addition salts of compounds I are obtained by treatment with a suitable acid or a suitable ion exchange reagent. Salts of compounds I can be converted in customary manner into the free compounds I, acid addition salts, for example, by treatment with a suitable basic agent or a suitable ion exchange reagent.

Salts of compounds I can be converted into different salts of compounds I in a manner known per se.

Depending on the procedure or reaction conditions, the compounds I having salt-forming, especially basic, properties, can be obtained in free form or in the form of salts.

Owing to the close relationship between the compounds I in free form and in the form of their salts, hereinbefore and hereinafter, the free compounds I and their salts are also to be understood as being the corresponding salts and free compounds I, respectively, where appropriate and where the context so allows.

The compounds I, including their salts of salt-forming compounds, can also be obtained in the form of their solvates, such as hydrates, and/or may include other solvents for example those used for crystallisation. Free compounds according to the invention are also to be understood as being the corresponding solvates, such as hydrates, where appropriate and where the context so allows.

Depending on the starting materials and procedures chosen, some of the compounds I and their salts may be in the form of one of the possible isomers or in the form of mixtures thereof, for example, depending on the number and absolute and relative configuration of the asymmetric carbon atoms, in the form of pure isomers, such as antipodes and/or diastereoisomers, or in the form of isomeric mixtures, such as enantiomeric mixtures, for example racemates, diastereoisomeric mixtures or racemate mixtures.

Resulting diastereoisomeric mixtures and racemate mixtures can be separated in known manner, for example by fractional crystallisation, into the pure diastereoisomers or racemates on the basis of the physico-chemical differences between their constituents. Resulting enantiomeric mixtures, such as racemates, can be resolved into the optical antipodes according to known methods, for example by recrystallisation from an optically active solvent, chromatography using chiral adsorbents, with the aid of suitable micro-organisms, by cleaving with specific immobilised enzymes, by way of the formation of inclusion compounds, for example using chiral crown ethers, only one enantiomer being complexed, or by conversion into diastereoisomeric salts, for example by reaction of a basic end product racemate with an optically active acid, such as a carboxylic acid, for example tartaric or malic acid, or sulfonic acid, for example camphorsulfonic acid, or by reaction of an acidic end product racemate with an optically active base, such as cinchonidine, cinchonine, quinine, phenethylamine, dehydrobietylamine, and separation of the diastereoisomeric mixture so obtained into the diastereoisomers, for example on the basis of their different solubilities, from which the desired enantiomer can be freed by the action of suitable agents. The more active enantiomer is advantageously isolated.

The invention relates also to those forms of the process according to which a compound obtainable as intermediate at any stage of the process is used as starting material and the remaining steps are carried out or a starting material is used in the form of a derivative or salt and/or its racemates or antipodes, or, especially, is formed under the reaction conditions.

In the process of the present invention, it is preferable to use those starting materials and intermediates that result in the compounds I described at the beginning as being especially valuable. The invention relates also to novel starting materials and intermediates for the preparation of the compounds I, their use and a process for their preparation, the variables $R_1$, $R_2$, $R_3$, $X_1$, $X_2$, $X_3$, $X_4$ Alk and Het and the rings A, B, C and D being as defined for the compounds I. The invention also relates especially to compounds of formulae II and IIa wherein $Z_1$ is, for example, cyano, the other variables being as defined above in each case.

The compounds I and their pharmaceutically acceptable salts can be used, preferably in the form of pharmaceutically acceptable compositions, in a method for the prophylactic and/or therapeutic treatment of the animal or human body, especially as antihypertensives or as agents for the treatment of glaucoma or for increasing the flow of the retinal ocular fluid.

The invention accordingly relates also to pharmaceutical compositions that comprise as active ingredients a compound I in free form or in the form of a pharmaceutically acceptable salt, and also to a process for their preparation.

These pharmaceutical compositions are compositions for enteral, such as oral, administration, and also rectal or parenteral administration, also for ophthalmic administration (that is to say, topical administration to the eye) to warm-blooded animals, the pharmacological active ingredient being comprised alone or together with customary pharmaceutical excipients. The pharmaceutical compositions comprise, for example, approximately from 0.1% to 100%, preferably from approximately 1% to approximately 60%, of the active ingredient. Pharmaceutical compositions for enteral or parenteral administration are, for example, in unit dose forms, such as dragées, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture of granules, if desired or necessary after the addition of suitable excipients, into tablets or dragée cores.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, gum tragacanth, methylcellulose and/or polyvinylpyrrolidone, and, if desired, disintegrators, such as the above-mentioned starches, also carboxymethyl starch, cross-linked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical compositions are dry-filled capsules consisting of gelatin, and also soft sealed capsules consisting of gelatin and a plasticizer, such as glycerol or sorbitol. The dry-filled capsules may contain the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical compositions, for example, suppositories that comprise a combination of the active ingredient and a suppository base. Suitable as suppository bases are, for example natural or synthetic triglycerides, paraffin hydrocarbons, polyethylene glycols and higher alkanols. It is also possible to use gelatin rectal capsules that comprise a combination of the active ingredient and a base material; suitable base materials are, for example, liquid triglycerides, polyethylene glycols and paraffin hydrocarbons.

Suitable for parenteral administration are especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and optionally also stabilisers.

The dose of the active ingredient may depend on various factors, such as the method of administration, species of warm-blooded animal, age and/or individual condition. In a normal case, the approximate estimated daily dose for a patient weighing approximately 75 kg is, in the case of oral administration, from approximately 10 mg to approximately 250 mg.

Corresponding ophthalmic compositions are advantageously administered topically to the eye, especially in the form of a solution, an ointment, a gel or a solid pad. Such compositions comprise the active ingredient, for example, in the range of from approximately 0.01 to approximately 10.0% by weight, preferably from approximately 0.5 to approximately 5.0 % by weight. Unit dose forms of the active ingredient are, for example, from approximately 0.001 to 5.0% by weight, especially from approximately 0.05 to approximately 2.0% by weight, preferably from approximately 0.1 to approximately 1.5% by weight, more especially from approximately 0.1 to approximately 1.0% by weight. The dose of the active ingredient may depend on various factors, such as method of administration, medical requirement, age and/or individual condition.

Customary pharmaceutically acceptable excipients and adjuvants known to the person skilled in the art, for example those of the type mentioned above, are used for corresponding ophthalmic compositions. Such compositions are prepared in a manner known per se. For example, the active ingredient is mixed with the corresponding excipients and/or adjuvants to form corresponding ophthalmic compositions. The active ingredient is preferably administered in the form of eye drops, the active ingredients being dissolved especially in a sterile aqueous isotonic solution which is, if necessary, buffered to the desired pH value.

The following Examples illustrate the invention described above; they are not, however, to limit the scope thereof in any way. Temperatures are given in degrees Celsius. The $R_f$ values are determined on silica gel layer plates (E. Merck—Item No. 5715) which are developed to the solvent system indicated in each case.

EXAMPLE 1

A solution of 0.82 g of N-[2-(2'-(1-tetrazol-5-yl)-phenyl)-quinolin-6-ylmethyl)]-N-valeroylvaline benzyl ester and 15 ml of 2N potassium hydroxide solution in 15 ml of ethanol is heated at 100° for 45 minutes. The cooled solution is acidified and concentrated by evaporation. The residue yields, after filtration through a millipore filter using methanol as solvent and removal of the solvent, N-[2-(2'-(1H-tetrazol-5-yl)-phenyl)-quinolin-6-ylmethyl]-N-valeroylvaline, $R_f$=0.19 ($CH_2Cl_2/CH_3OH$ (4:1)).

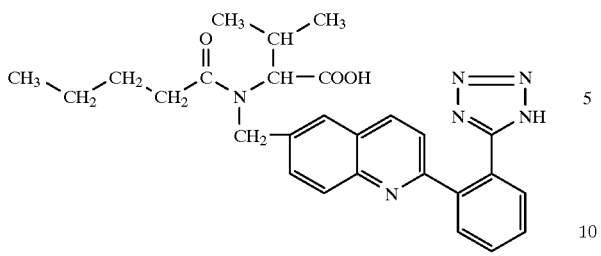

The starting material can be prepared, for example, as follows:

a) A solution of 11.94 g of trimethyltin chloride in 10 ml of dimethoxyethane is added to a mixture, maintained at 0°, of 4.14 g of sodium in 40 ml of dimethoxyethane and stirred for 3 hours at 0°. The green-yellow suspension formed is separated from the excess sodium, and a solution of 8.88 g of 2-chloro-6-methylquinoline (O. Fischer, Berichte 32, 1305) in 30 ml of tetrahydrofuran is added dropwise at 0°. After stirring for 3 hours, the batch is heated to room temperature. The mixture is diluted with 50 ml of ether and washed twice with 10 ml of water each time. The ether phase is dried over $Na_2SO_4$, freed of the solvent and distilled in a bulb tube, 6-methyl-2-trimethylstannylquinoline passes over at 200° and 0.2 mbar.

b) 0.40 g of tetrakis(triphenylphosphine)palladium (Fluka 87645) is added to a solution of 10.66 g of 6-methyl-2-trimethylstannylquinoline and 7.98 g of 2-iodobenzonitrile in 75 ml of toluene and the batch is heated under reflux for 27 hours. The reaction mixture is concentrated by evaporation in vacuo and diluted with 90 ml of ether and crystallised. By filtering with suction, 6-methyl-2-(2'-cyanophenyl)-quinoline, m.p. 154–155°, is obtained.

c) A mixture of 4.89 g of 6-methyl-2-(2'-cyanophenyl)-quinoline, 4.04 g of N-bromosuccinimide and 0.09 g of azoisobutyronitrile in 100 ml of carbon tetrachloride is heated at 110° for 6 hours, 20 ml of 2 N sodium hydroxide solution are then added to the cooled reaction mixture and the batch is extracted once with 100 ml and then twice with 50 ml each time of $CH_2Cl_2$. The organic phases yield, after customary treatment, 6-bromomethyl-2-(2'-cyanophenyl)-quinoline, m.p. 162–166°.

d) A solution of 4.44 g of valine benzyl ester toluenesulfonic acid salts, 5.17 g of Hünig base and 3.23 g of 6-bromomethyl-2-(2'-cyanophenyl)-quinoline in 20 ml of dimethylformamide is heated at 80° C. for 1 hour. The solvent is then removed and the crude product is dissolved in 200 ml of ethyl acetate. The organic phase is washed twice with 50 ml of water each time and once with 50 ml of saturated $NaHCO_3$ solution and once with 50 ml of brine. The washing phases are re-extracted with 50 ml of ethyl acetate. The combined organic phase are treated in the customary manner and yield N-[2-(2'-cyanophenyl)-quinolin-6-ylmethyl]-valine benzyl ester, $R_f$=0.21 ($CH_2Cl_2/CH_3OH$ (99:1)), which is further processed in the crude state.

e) A solution of 4.79 g of N-[2-(2'-cyanophenyl)-quinolin-6-ylmethyl]-valine benzyl ester, 2.07 ml of triethylamine and 1.80 ml of valeroyl chloride in 100 ml of $CH_2Cl_2$ is stirred for 1 hour at room temperature and then washed twice with 50 ml of water each time, and the washing phases are re-extracted with 50 ml of $CH_2Cl_2$. The organic phases yield, after customary treatment, N-[2-(2'-cyanophenyl)-quinolin-6-ylmethyl]-N-valeroylvaline benzyl ester, $R_f$=0.23 ($CH_2Cl_2/CH_3OH$ (99:1)).

f) A solution of 5.33 g of N-[2-(2'-cyanophenyl)-quinolin-6-ylmethyl]-N-valeroylvaline benzyl ester and 13 g of tributylin azide in 100 ml of xylene is heated under reflux for 5 hours. The cooled solution is stirred with 50 ml of 2N sodium hydroxide solution of 30 minutes. The aqueous phase is acidified and extracted three times with 50 ml of $CH_2Cl_2$ each time. The crude product obtained after proceeding in the customary manner yields, after chromatography on silica gel 60 (40–63 μm—Merck Item No. 9385) using $CH_2Cl_2/CH_3OH$ (95:5) as eluant, N-[2-(2'-(1H-tetrazol-5-yl)-phenyl)-quinolin-6-ylmethyl]-N-valeroylvaline benzyl ester, $R_f$=0.48 ($CH_2Cl_2/CH_3OH$ (4:1)).

EXAMPLE 2

Analogously to Example 1, 0.84 g of N-[2-(2'-(1H-tetrazol-5-yl)-phenyl)-quinolin-6-ylmethyl)]-N-valeroyl-1-aminomethylcyclopentane-1-carboxylic acid ethyl ester and 5 ml of 2N potassium hydroxide solution are dissolved in 10 ml of ethanol and heated at 100° for 2.5 hours. Working-up is effected by drying with $Na_2SO_4$, filtering and removing the solvent using a rotary evaporator under reduced pressure and yields N-[2-(2'-(1H-tetrazol-5-yl)-phenyl)-quinolin-6-ylmethyl]-N-valeroyl-1-aminomethylcyclopentane-1-carboxylic acid, $R_f$=0.14 ($CH_2Cl_2/CH_3OH$ (4:1)).

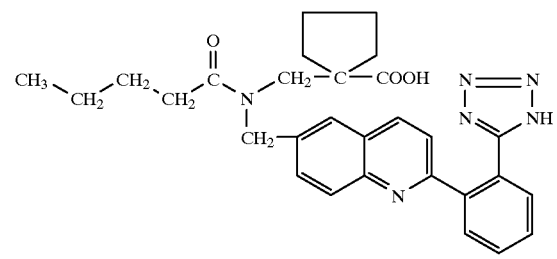

The starting material can be prepared, for example, as follows:

a) 1-Aminomethylcyclopentane-1-carboxylic acid ethyl ester is obtained by hydrogenating 33 g of 1-cyanocyclopentane-1-carboxylic acid ethyl ester (Alfred Bader Chemicals) in 330 ml of ethanol, which contains approximately 4% ammonia, in the presence of 10 g of Raney nickel at 45° C. and under normal pressure. After filtering off from the catalyst and removing the solvent in vacuo, the product is obtained by distillation, b.p. 71–74° at 0.75 mbar.

b) A solution of 1.03 g of 1-aminomethylcyclopentane-1-carboxylic acid ethyl ester, 0.68 ml of N-methylmorpholine and 1.94 g of 6-bromomethyl-2-(2'-cyanophenyl)quinoline is brought to the melt by heating and, after 20 minutes, is diluted with 60 ml of ethyl acetate. The solution is washed twice with 20 ml of saturated $NaHCO_3$ solution each time, dried over $Na_2SO_4$ and freed of the solvent. The resulting crude product yields, after chromatography on silica gel 60 (40–63 μm) using $CH_2Cl_2/CH_3OH$ (98:2) as eluant, N-[2-(2'-cyanophenyl)-quinolin-6-ylmethyl]-1-aminomethylcyclopentane-1-carboxylic acid ethyl ester, $R_f$=0.28 ($CH_2Cl_2/CH_3OH$ (95:5)).

c) Analogously to Example 1 e), N-[2-(2'-cyanophenyl)-quinolin-6-ylmethyl]-N-valeroyl-1-aminomethylcyclopentane-1-carboxylic acid ethyl ester, $R_f$=0.64 ($CH_2Cl_2/CH_3OH$ (95:5)) is obtained.

d) Analogously to Example 1 f), after chromatography on silica gel 60 (40–63 μm) using $CH_2Cl_2/CH_3OH$ (9:1) as eluant, N-[2-(2'-(1H-tetrazol-5-yl)-phenyl)-quinolin-6-yl-methyl]-N-valeroyl-1-aminomethylcyclopentane-1-carboxylic acid ethyl ester, $R_f$=0.43 ($CH_2Cl_2/CH_3OH$ (4:1)), is obtained.

EXAMPLE 3

A solution of 1.73 g of N-[2-(2'-(1H-tetrazol-5-yl)-phenyl)-quinolin-6-ylmethyl]-N-valeroyl-2-aminomethyl-2-ethylbutyric acid tert-butyl ester in 10 ml of trifluoroacetic acid is stirred at room temperature for 45 minutes, diluted with toluene and concentrated by evaporation. The crude product yields, after chromatography on silica gel 60 (40–63 μm) using $CH_2Cl_2/CH_3OH$ (95:5) as eluant, N-[2-(2'-(1H-tetrazol-5-yl)-phenyl)-quinolin-6-ylmethyl]-N-valeroyl-2-aminomethyl-2-ethylbutyric acid, $R_f$=0.38 ($CH_2Cl_2/CH_3OH$ (4:1)).

The starting material can be prepared, for example, as follows:

a) A mixture of 13.06 g of cyanoacetic acid tert-butyl ester (Lancester Synthesis Ltd., LAN-0123), 20.7 ml of bromoethane, 0.96 g of n-tetrabutylammonium bromide, 58 ml of potassium hydroxide solution and 50 ml of $CH_2Cl_2$ is stirred at room temperature for 23 hours. The phases are separated and the aqueous phase is extracted three times with 50 ml of ether each time. All of the organic phases are combined and washed three times with 50 ml of water each time. The crude product obtained after working up as described in Example 2 yields 2-cyano-2-ethylbutyric acid tert-butyl ester after distillation in vacuo.

b) 29.21 g of 2-cyano-2-ethylbutyric acid tert-butyl ester, dissolved in 300 ml of ethanol, which contains 4% ammonia, are hydrogenated after normal pressure at 40° in the presence of 6 g of Raney nickel. After separating off from the catalyst, the batch is concentrated by evaporation in vacuo and the liquid that remains is distilled in vacuo to yield 2-aminomethyl-2-ethylbutyric acid tert-butyl ester, boiling point 65° at 0.6 mbar.

c) A solution of 1.98 g of 2-aminomethyl-2-ethylbutyric acid tert-butyl ester, 1.4 ml of N-methylmorpholine and 2.91 g of 6-bromomethyl-2-(2'-cyanophenyl)-quinoline is heated at 100° C. for 1.5 hours. The mixture is taken up in 100 ml of ethyl acetate and washed with 50 ml of water and 50 ml of saturated $NaHCO_3$ solution. The crude product obtained after proceeding in the customary manner yields, after chromatography on silica gel 60 (40–63 μm) using $CH_2Cl_2/CH_3OH$ (98:2) as eluant, N-[2-(2'-cyanophenyl)-quinolin-6-ylmethyl]-2-aminomethyl-2-ethylbutyric acid tert-butyl ester, $R_f$=0.40 ($CH_2Cl_2/CH_3OH$ (95:5)).

d) Analogously to Example 1 e), N-[2-(2'-cyanophenyl)-quinolin-6-ylmethyl]-N-valeroyl-2-aminomethyl-2-ethylbutyric acid tert-butyl ester, $R_f$=0.59 ($CH_2Cl_2/CH_3OH$ (95:5)), is obtained.

e) Analogously to Example 1 f), N-[2-(2'-(1H-tetrazol-5-yl)-phenyl)-quinolin-6-ylmethyl]-N-valeroyl-2-aminomethyl-2-ethylbutyric acid tert-butyl ester, $R_f$=0.55 ($CH_2Cl_2/CH_3OH$ (4:1)), is obtained.

EXAMPLE 4

A solution of 1.426 g of N-[2-(2'-(1H-tetrazol-5-yl)-phenyl)-5-ylmethylbenzo[b]thiophene]-N-valeroyl-2-aminomethyl-2-ethylbutyric acid tert-butyl ester in 10 ml of trifluoroacetic acid is stirred for 30 minutes at room temperature. The crude product obtained after removing the solvent yields, after chromatography on silica gel 60 (40–63 μm) using $CH_2Cl_2/CH_3OH$ (95:5) as eluant, N-[2-(2'-(1H-tetrazol-5-yl)-phenyl)-benzo[b]thiophen-5-ylmethyl]-N-valeroyl-2-aminomethyl-2-ethylbutyric acid, $R_f$=0.39 ($CH_2Cl_2/CH_3OH$ (4:1)).

The starting material can be prepared, for example, as follows:

a) A solution of 7.411 g of 5-methylbenzo[b]thiophene (Maybridge, Chemical Co. Ltd., 11-78) in 35 ml of ether is added dropwise at 0° to a mixture of 40 ml of 1.5N butylithium in hexane and 40 ml of ether. After 30 minutes, a solution of 9.963 g of trimethyltin chloride in 50 ml of ether is also added dropwise at 0°. After stirring for 1 hour at 0°, 50 ml of 5% ammonium chloride solution are added. The product is obtained by extracting with 100 ml and 150 ml of ether. Distillation at 0.15 mbar and 100–106° yields 5-methyl-2-trimethylstannylbenzo[b]thiophene.

b) A solution of 12.84 g of 5-methyl-2-trimethylstannylbenzo[b]thiophene, 9.39 g of 2-iodobenzonitrile and 0.464 g of tetrakis(triphenylphosphine)palladium in 120 ml of toluene is heated under reflux for 6.5 hours. After removing the solvent, the batch is diluted with 30 ml of ether, and 2-(2'-cyanophenyl)-5-methylbenzo[b]thiophene. m.p. 152–153°, is obtained by filtering off with suction.

c) A mixture of 5.00 g of 2-(2'-cyanophenyl)-5-methylbenzo[b]thiophene, 4.04 g of N-bromosuccinimide and 0.09 g of azoisobutyronitrile in 100 ml of carbon tetrachloride is heated under reflux for 5 hours. After the addition of 50 ml of $CH_2Cl_2$, the batch is extracted twice with 20 ml of 2N sodium hydroxide solution each time; the alkaline phases are re-extracted with 50 ml of $CH_2Cl_2$. The organic phase yield, after working up in accordance with Example 2, 5-bromomethyl-2-(2'-cyanophenyl)-benzo[b]thiophene. m.p. 108–110°.

d) A mixture of 5.03 g of 2-aminomethyl-2-ethylbutyric acid tert-butyl ester and 3.283 g of 5-bromomethyl-2-(2'-cyanophenyl)-benzo[b]thiophene is stirred for 15 minutes at 100° and, after cooling, is taken up in 100 ml of ethyl acetate. The crude product obtained after washing with 50 ml of $NaHCO_3$ solution and 50 ml of water and after working up in accordance with Example 2 yields, after chromatography on silica gel 60 (40–63 μm) using $CH_2Cl_2/CH_3OH$ (99:1) as eluant, N-[2-(2'-cyanophenyl)-benzo[b]thiophen-5-yl-methyl]-2-aminomethyl-2-ethylbutyric acid tert-butyl ester, $R_f$=0.48 ($CH_2Cl_2/CH_3OH$ (95:5)).

e) Analogously to Example 1 e), N-[2-(2'-cyanophenyl)-benzo[b]thiophen-5-ylmethyl]-N-valeroyl-2-aminomethyl-2-ethylbutyric acid tert-butyl ester, $R_f$=0.64 ($CH_2Cl_2/CH_3OH$ (95:5)), is obtained.

f) Analogously to Example 1 f), N-[2-(2'-(1H-tetrazol-5-yl)-phenyl)-5-ylmethylbenzo[b]thiophene]-N-valeroyl-2-aminomethyl-2-ethylbutyric acid tert-butyl ester, $R_f$=0.42 ($CH_2Cl_2/CH_3OH$ (4:1)), is obtained.

EXAMPLE 5

A solution of 2.41 g of N-[3-bromo-2-(2'-ethoxycarbonylphenyl)-benzo[b]thiophen-5-ylmethyl]-N-valeroylvaline benzyl ester and 20 ml of 2N potassium hydroxide solution in 20 ml of ethanol is heated under reflux for 22 hours. The cooled solution is acidified and concentrated by evaporation. The residue yields, after chromatography on silica gel 60 (40–63 μm) using $CH_2Cl_2/CH_3OH$ (95:5) as eluant, N-[3-bromo-2-(2'-carboxyphenyl)-benzo[b]thiophen-5-ylmethyl]-N-valeroylvaline, $R_f$=0.44 ($CH_2Cl_2/CH_3OH$ (4:1)).

The starting material can be prepared, for example, as follows:

a) A solution of 8.59 g of 5-methyl-2-trimethylstannylbenzo[b]thiophene, 7.62 g of 2-iodobenzoic acid ethyl ester and 0.31 g of tetrakis(triphenylphosphine) palladium in 70 ml of toluene is heated under reflux for 11 hours. The residue remaining after concentration by evaporation yields, after chromatography on silica gel 60 (40–63 μm) using hexane/ethyl acetate (9:1) as eluant, 2-(2'-ethoxycarbonylphenyl)-5-methylbenzo[b]thiophene, $R_f$=0.33 (hexane/ethyl acetate (9:1)).

b) A mixture of 7.97 g of 2-(2'-ethoxycarbonylphenyl)-5-methylbenzo[b]thiophene, 4.58 g of N-bromosuccinimide and 0.10 g of azoisobutyronitrile in 100 ml of carbon tetrachloride is heated under reflux for 3 hours. The cooled mixture is diluted with 50 ml of $CH_2Cl_2$ and extracted with 20 ml of 2N sodium hydroxide solution. The alkaline phase is extracted with 50 ml of $CH_2Cl_2$. The organic phases yield, after working up in accordance with Example 2, a crude product from which there is obtained, after chromatography on silica gel 60 (40–63 μm) using hexane/ethyl acetate (9:1), 3-bromo-5-bromomethyl-2-(2'-ethoxycarbonylphenyl)-benzo[b]thiophene, $R_f$=0.26 (hexane/ethyl acetate (9:1).

c) Analogously to Example 1 d), N-[3-bromo-2-(2'-ethoxycarbonylphenyl)-benzo[b]thiophen-5-ylmethyl]-N-valine benzyl ester, $R_f$=0.76 ($CH_2Cl_2/CH_3OH$ (95:5)), is obtained.

d) Analogously to Example 1 e), N-[3-bromo-2-(2'-ethoxycarbonylphenyl)-5-ylmethylbenzo[b]thiophene]-N-valeroylvaline benzyl ester, $R_f$=0.74 ($CH_2Cl_2/CH_3OH$ (95:5)), is obtained.

EXAMPLE 6

A solution of 1.42 g of N-[2-(2'-(1H-tetrazol-5-yl)-phenyl)-benzofuran-5-ylmethyl]-N-valeroyl-2-aminomethyl-2-ethylbutyric acid ethyl ester and 10 ml of 2N potassium hydroxide solution in 20 ml of ethanol is stirred at room temperature for 48 hours. After removing the solvent, the batch is acidified and extracted twice with 50 ml of $CH_2Cl_2$ each time. The crude product obtained after working up in accordance with Example 2 yields, after chromatography on silica gel 60 (40–63 μm) using $CH_2Cl_2/CH_3OH$ (95:5) as eluant, N-[2-(2'-(1H-tetrazol-5-yl)-phenyl-benzofuran-5-ylmethyl]-N-valeroyl-2-aminomethyl-2-ethylbutyric acid $R_f$=0.14 ($CH_2Cl_2/CH_3OH$ (4:1)).

The starting material can be prepared, for example, as follows:

a) A mixture of 20 g of 2-hydroxy-5-methylbenzaldehyde, 28 g of α-bromo-o-tolunitrile and 22 g of potassium carbonate in 220 ml of ethanol is heated under reflux for 2 hours. The cooled mixture is filtered and concentrated by evaporation. The residue is dissolved in 300 ml of $CH_2Cl_2$ and washed with 80 ml of saturated $NaHCO_3$ solution and twice with 100 ml of water each time. The aqueous phases are re-extracted with 100 ml of $CH_2Cl_2$. The organic phases yield, after working up in accordance with Example 2, a crude product from which there is obtained, by dissolving in 500 ml of $CH_2Cl_2$, stirring with 100 g of silica gel 60, filtering with suction and removing the solvent, 2-formyl-3-methylphenyl-2'-cyano-1'-benzyl ether, $R_f$=0.25 ($CH_2Cl_2$).

b) A solution of 23.3 g of 2-formyl-3-methylphenyl-2'-cyano-1'-benzyl ether in 230 ml of dimethylformamide is mixed with 17.7 ml of a 5.25M solution of sodium methanolate in methanol and the mixture is heated at 125° for 1.5 hours. After cooling, the solvent is removed, and the residue is taken up in 1500 ml of ether and 300 ml of water and acidified. The organic phase is washed twice with 200 ml of water each time and, after working up in accordance with Example 2, yields a crude product from which, after chromatography on silica gel 60 (40–63 μm) using $CH_2Cl_2$ as eluant, 2-(2'-cyanophenyl)-5-ylmethylbenzofuran, $R_f$=0.53 ($CH_2Cl_2$), is obtained.

c) A mixture of 3.1 g of 2-(2'-cyanophenyl)-5-methylbenzofuran, 2.6 g of N-bromosuccinimide and 0.05 g of azoisobutyronitrile in 50 ml of carbon tetrachloride is stirred at 110° for 4 hours. The cooled mixture is filtered and the filtrate is washed with 15 ml of 1N sodium hydroxide solution, 30 ml of 0.1N hydrochloric acid and twice with 30 ml of water each time. The organic phase yields, after customary treatment, 5-bromomethyl-2-(2'-cyanophenyl)-benzofuran, $R_f$=0.25 (hexane/ethyl acetate (95:5)).

d) A solution of 3.5 g of 5-bromomethyl-2-(2'-cyanophenyl)-benzofuran, 2.33 g of 2-aminomethyl-2-ethylbutyric acid ethyl ester, 1.89 ml of triethylamine and 0.27 g of 4-dimethylaminopyridine in 50 ml of tetrahydrofuran is stirred at room temperature for 30 hours. The reaction mixture is filtered and freed of the solvent. The residue is taken up in 200 ml of $CH_2Cl_2$ and washed with 100 ml of saturated $NaHCO_3$ solution. The organic phase yields, after customary treatment and chromatography on silica gel 60 (40–63 μm) using hexane/ethyl acetate (5:1) as eluant, N-[2-(2'-cyanophenyl)-benzofuran-5-ylmethyl]-2-aminomethyl-2-ethylbutyric acid ethyl ester, $R_f$=0.47 ($CH_2Cl_2/CH_3OH$ (95:5)).

e) Analogously to Example 1 e), N-[2-(2'-cyanophenyl)-benzofuran-5-ylmethyl]-N-valeroyl-2-aminomethyl-2-ethylbutyric acid ethyl ester, $R_f$=0.61 ($CH_2Cl_2/CH_3OH$ (95:5)), is obtained.

f) Analogously to Example 1 f), N-[2-(2'-(1H-tetrazol-5-yl)-phenyl)-benzofuran-5-ylmethyl]-N-valeroyl-2-aminomethyl-2-ethylbutyric acid ethyl ester, $R_f$=0.50 ($CH_2Cl_2/CH_3OH$ (4:1)), is obtained.

EXAMPLE 7

A solution of 0.33 g of N-[2-(2'-(1H-tetrazol-5-yl)-phenyl)-benzofuran-5-ylmethyl]-N-valeroyl-1-aminomethylcyclopentane-1-carboxylic acid ethyl ester and 2.0 ml of potassium hydroxide solution in 4.0 ml of ethanol is heated under reflux for 2.5 hours. The cooled solution is acidified and concentrated, and 20 ml of $CH_2Cl_2$ and 1 ml of water are added. Extraction with another 15 ml of $CH_2Cl_2$ and customary treatment of the organic phases yields N-[2-(2'-(1H-tetrazol-5-yl)-phenyl)-benzofuran-5-ylmethyl]-N-valeroyl-1-aminomethylcyclopentane-1-carboxylic acid, $R_f$=0.30 ($CH_2Cl_2/CH_3OH$ (4:1)).

The starting material can be prepared, for example, as follows:

a) A solution of 0.312 g of 5-bromomethyl-2-(2'-cyanophenyl)-benzofuran, 0.208 g of 1-aminomethylcyclopentane-1-carboxylic acid ethyl ester, 0.17 ml of triethylamine and 0.024 g of 4-dimethylaminopyridine in 5.0 ml of tetrahydrofuran is stirred at room temperature for 20 hours. The mixture is freed of the solvent and taken up in 20 ml of ethyl acetate and washed with 10 ml of saturated $NaHCO_3$ solution. The organic phase yields, after customary treatment and chromatography on silica gel 60 (40–63 μm) using hexane/ethyl acetate (9:1) as eluant, N-[2-(2'-cyanophenyl)-benzofuran-5-ylmethyl]-1-aminomethylcyclopentane-1-carboxylic acid ethyl ester, $R_f$=0.27 ($CH_2Cl_2$).

b) Analogously to Example 1 e), N-[2-(2'-cyanophenyl)-benzofuran-5-ylmethyl]-N-valeroyl-1-aminomethylcyclopentane-1-carboxylic acid ethyl ester, $R_f$=0.70 ($CH_2Cl_2/CH_3OH$ (95:5)), is obtained.

c) Analogously to Example 1 f), N-2-[2'-(1H-tetrazol-5-yl)-phenyl)-benzofuran-5-ylmethyl]-N-valeroyl-1-aminomethylcyclopentane-1-carboxylic acid ethyl ester, $R_f$=0.50 ($CH_2Cl_2/CH_3OH$ (4:1)), is obtained.

EXAMPLE 8

A solution of 0.733 g of N-[2-(2'-(1H-tetrazol-5-yl)-phenyl)-benzofuran-5-ylmethyl]-N-valeroylvaline benzyl ester and 4 ml of 2N sodium hydroxide solution in 15 ml of ethanol is heated under reflux for 1.5 hours. The cooled solution is acidified and freed of the solvent. The residue yields, after chromatography on silica gel 60 (40–63 μm) using $CH_2Cl_2/CH_3OH$ (9:1) as eluant, N-[2-(2'-(1H-tetrazol-5-yl)-phenyl)-benzofuran-5-ylmethyl]-N-valeroylvaline, $R_f$=0.40 ($CH_2Cl_2/CH_3OH$ (4:1)).

The starting material can be prepared, for example, as follows:

a) A solution of 4.44 g of valine benzyl ester toluenesulfonic acid salt, 6.8 ml of Hünig base and 3.12 g of 5-bromomethyl-2-(2'-cyanophenyl)-benzofuran in 20 ml of dimethylformamide is heated at 80° for one hour. Working up analogously to Example 2 a) yields N-[2-(2'-cyanophenyl)-benzofuran-5-ylmethyl]-valine benzyl ester, $R_f$=0.20 ($CH_2Cl_2/CH_3OH$ (99:1)).

b) Analogously to Example 1 e), N-[2-(2'-cyanophenyl)-benzofuran-5-ylmethyl]-N-valeroylvaline benzyl ester, $R_f$=0.25 ($CH_2Cl_2/CH_3OH$ (99:1)), is obtained.

c) Analogously to Example 1 f), N-[2-(2'-(1H-tetrazol-5-yl)-phenyl)-benzofuran-5-ylmethyl]-N-valeroylvaline benzyl ester, $R_f$=0.55 ($CH_2Cl_2/CH_3OH$ (4:1)), is obtained.

EXAMPLE 9

A solution of 3.64 g of N-[2-(2'-(1H-tetrazol-5-yl)-phenyl)-benzo[b]-thiophen-5-ylmethyl]-N-valeroyl-1-aminomethylcyclopentane-1-carboxylic acid ethyl ester and 13.4 ml of 2N sodium hydroxide solution in 33 ml of ethanol is heated under reflux for 17 hours. The residue yields, after chromatography on silica gel 60 (40–63 μm) using $CH_2Cl_2/CH_3OH$ (9:1) as eluant, N-[2-(2'-(1H-tetrazol-5-yl)-phenyl)-5-ylmethylbenzo[b]thiophene]-N-valeroyl-1-aminomethylcyclopentane-1-carboxylic acid, $R_f$=0.55 ($CH_2Cl_2/CH_3OH$ (4:1)).

The starting material can be prepared, for example, as follows:

a) A mixture of 3.28 g of 5-bromomethyl-2-(2'-cyanophenyl)-benzo[b]thiophene and 4.28 g of 1-aminomethylcyclopentane-1-carboxylic acid ethyl ester is heated at 100° for 30 minutes. The cooled mixture is taken up in 100 ml of ethyl acetate and washed with 50 ml of saturated $NaHCO_3$ solution and 50 ml of water. The washing phase was re-extracted with 50 ml of ethyl acetate. The organic phase yield, after customary treatment and chromatography on silica gel 60 (40–63 μm) using $CH_2Cl_2/CH_3OH$ (98:2) as eluant, N-[2-(2'-cyanophenyl)-benzo[b]thiophen-5-ylmethyl]-1-aminomethylcyclopentane-1-carboxylic acid ethyl ester, $R_f$=0.38 ($CH_2Cl_2/CH_3OH$ (95:5)).

b) Analogously to Example 1 e), N-[2-(2'-cyanophenyl)-benzo[b]thiophen-5-ylmethyl]-N-valeroyl-1-aminomethylcyclopentane-1-carboxylic acid ethyl ester, $R_f$=0.67 ($CH_2Cl_2/CH_3OH$ (95:5)), is obtained.

c) Analogously to Example 1 f), N-[2-(2'-(1H-tetrazol-5-yl)-phenyl)-benzo[b]thiophen-5-ylmethyl]-N-valeroyl-1-aminomethylcyclopentane-1-carboxylic acid ethyl ester, $R_f$=0.57 ($CH_2Cl_2/CH_3OH$ (4:1)), is obtained.

EXAMPLE 10

A solution of 1.87 g of N-[2-(2'-(1H-tetrazol-5-yl)-phenyl)-5-ylmethylbenzo[b]thiophene]-N-valeroylvaline benzyl ester and 8 ml of 2N sodium hydroxide solution in 25 ml of ethanol is heated under reflux for 1.5 hours. The cooled solution is acidified and concentrated by evaporation. The residue yields, after chromatography on silica gel 60 (40–63 μm) using $CH_2Cl_2/CH_3OH$ (9:1) as eluant, N-[2-(2'-(1H-tetrazol-5-yl)-phenyl)-benzo[b]thiophen-5-ylmethyl]-N-valeroylvaline, $R_f$=0.31 ($CH_2Cl_2/CH_3OH$ (4:1)).

The starting material can be prepared, for example, as follows:

a) Analogously to Example 1 d), after chromatography on silica gel 60 (40–63 μm) using $CH_2Cl_2/CH_3OH$ (9:1) as eluant, N-[2-(2'-cyanophenyl)-benzo[b]thiophen-5-ylmethyl]-N-valeroylvaline benzyl ester, $R_f$=0.21 ($CH_2Cl_2/CH_3OH$ (99:1)), is obtained.

b) Analogously to Example 1 e), N-[2-(2'-(1H-tetrazol-5-yl)-phenyl)-5-ylmethylbenzo[b]thiophene]-N-valeroylvaline benzyl ester, $R_f$=0.31 (hexane/ethyl acetate (2:1)), is obtained.

c) Analogously to Example 1 f), N-[1-(2'-(1H-tetrazol-5-yl)-phenyl)-5-ylmethylbenzo[b]thiophene]-N-valeroylvaline benzyl ester, $R_f$=0.55 ($CH_2Cl_2/CH_3OH$ (4:1)), is obtained.

EXAMPLE 11

A solution of 2.15 g of N-[3-bromo-2-(2'-ethoxycarbonylphenyl)-benzo[b]thiophene-5-ylmethyl]-N-valeroyl-1-aminomethylcyclopentane-1-carboxylic acid ethyl ester and 20 ml of 2N potassium hydroxide solution in 20 ml of ethanol is heated under reflux for two days. Working up analogously to Example 7 yields N-[3-bromo-2-(2'-carboxyphenyl)-benzo[b]thiophen-5-ylmethyl]-N-valeroyl-1-aminomethylcyclopentane-1-carboxylic acid, $R_f$=0.66 ($CH_2Cl_2/CH_3OH$ (4:1)).

The starting material can be prepared, for example, as follows:

a) Analogously to Example 1 d), N-[3-bromo-2-(2'-ethoxycarbonylphenyl)-benzo[b]thiophen-5-ylmethyl]-1-aminomethylcyclopentane-1-carboxylic acid ethyl ester, $R_f$=0.41 ($CH_2Cl_2/CH_3OH$ (95:5)), is obtained.

b) Analogously to Example 1 e), N-[3-bromo-2-(2'-ethoxycarbonylphenyl)-benzo[b]thiophen-5-ylmethyl]-N-valeroyl-1-aminomethylcyclopentane-1-carboxylic acid ethyl ester, $R_f$=0.63 ($CH_2Cl_2/CH_3OH$ (95:5)), is obtained.

EXAMPLE 12

A solution of 5.20 g of N-[2-(2'-(1H-tetrazol-5-yl)-phenyl)-benzofuran-5-ylmethyl]N-valeroyl-1-aminomethylcyclohexane-1-carboxylic acid ethyl ester and 50 ml of 2N potassium hydroxide solution in 100 ml of ethanol is heated under reflux for 18 hours. The cooled solution is acidified and concentrated by evaporation. The residue yields, after chromatography on silica gel 60 (40–63

μm) using CH$_2$Cl$_2$/CH$_3$OH (95:5) as eluant, N-[2-(2'-(1H-tetrazol-5-yl)-phenyl)-benzofuran-5-ylmethyl]-N-valeroyl-1-aminomethylcyclohexane-1-carboxylic acid, R$_f$=0.50 (CH$_2$Cl$_2$/CH$_2$OH (4:1)).

The starting material can be prepared, for example, as follows:

a) 1-Aminomethylcyclohexane-1-carboxylic acid ethyl ester is obtained by hydrogenating 72.08 g of 1-cyanocyclohexane-1-carboxylic acid ethyl ester (T. Kurihara et al. Tet. Lett. 1976, 2455) in 600 ml of ethanol, which contains approximately 4% ammonia, in the presence of 20 g of Raney nickel at 45° and under normal pressure. After removing the catalyst and the solvent, the product is obtained by distillation, boiling point 72–75° at 0.3 mbar.

b) Analogously to Example 9 a), N-[2-(2'-cyanophenyl)-benzofuran-5-ylmethyl]-1-aminomethylcyclohexane-1-carboxylic acid ethyl ester, R$_f$=0.36 (CH$_2$Cl$_2$/CH$_3$OH (95:5)), is obtained.

c) Analogously to Example 1 e), N-[2-(2'-cyanophenyl)-benzofuran-5-ylmethyl]-N-valeroyl-1-aminomethylcyclohexane-1-carboxylic acid ethyl ester, R$_f$=0.64 (CH$_2$Cl$_2$/CH$_3$OH (95:5)), is obtained.

d) Analogously to Example 1 f), N-[2-(2'-(1H-tetrazol-5-yl)-phenyl)-benzofuran-5-ylmethyl]-N-valeroyl-1-aminomethylcyclohexane-1-carboxylic acid ethyl ester, R$_f$=0.52 (CH$_2$Cl$_2$/CH$_3$OH (4:1)), is obtained.

EXAMPLE 13

It is possible to obtain in an analogous manner, for example as described in one of Examples 1–12:

N-[2-(2'-(tetrazol-5-yl)-phenyl)-naphthalen-6-ylmethyl]-N-valeroylvaline;

N-[2-(2'-(tetrazol-5-yl)-phenyl)-naphthalen-6-ylmethyl]-N-valeroyl-1-aminomethylcyclopentane-1-carboxylic acid;

N-[2-(2'-(tetrazol-5-yl)-phenyl)-naphthalen-6-ylmethyl]-N-valeroyl-1-aminocyclopentane-1-carboxylic acid;

N-[2-(2'-(tetrazol-5-yl)-phenyl)-naphthalen-6-ylmethyl]-N-valeroyl-1-aminocyclohexane-1-carboxylic acid;

N-[2-(2'-carboxyphenyl)-naphthalen-6-ylmethyl]-N-valeroyl-1-aminomethylcyclopentane-1-carboxylic acid;

N-[2-(2'-(tetrazol-5-yl)-phenyl)-naphthalen-6-ylmethyl]-N-valeroyl-2-aminomethyl-2-ethylbutyric acid;

N-[2-(2'-(tetrazol-5-yl)-phenyl)-naphthalen-6-ylmethyl]-N-valeroyl-2-aminopropionic acid;

N-[2-(2'-(tetrazol-5-yl)-phenyl)-naphthalen-6-ylmethyl]-N-valeroyl-2-amino-2-methylpropionic acid;

N-[2-(2'-(tetrazol-5-yl)-phenyl)-naphthalen-6-ylmethyl]-N-valeroyl-1-aminomethylcyclohexane-1-carboxylic acid;

N-[2-(2'-(tetrazol-5-yl)-phenyl)-naphthalen-6-ylmethyl]-N-butyryl-1-aminomethylcyclopentane-1-carboxylic acid;

N-[2-(2'-carboxyphenyl)-6-ylmethyl]-N-butyryl-1-aminomethylcyclopentane-1-carboxylic acid;

N-[2-(2'-(tetrazol-5-yl)-phenyl)-quinolin-6-ylmethyl]-N-cyclopropylcarbonylvaline;

N-[2-(2'-(tetrazol-5-yl)-phenyl)-quinolin-6-ylmethyl]-N-cyclopropylcarbonyl-1-aminomethylcyclopentane-1-carboxylic acid;

N-[2-(2'-(tetrazol-5-yl)-phenyl)-quinolin-6-ylmethyl]-N-cyclopropylcarbonyl-2-aminomethyl-2-ethylbutyric acid;

N-[2-(2'-(tetrazol-5-yl)-phenyl)-quinolin-6-ylmethyl]-N-cyclopropylcarbonyl-1-aminomethylcyclohexane-1-carboxylic acid;

N-[2-(2'-(tetrazol-5-yl)-phenyl)-naphthalen-6-ylmethyl]-N-propoxycarbonylvaline;

N-[2-(2'-(tetrazol-5-yl)-phenyl)-naphthalen-6-ylmethyl]-N-propoxycarbonyl-1-aminomethylcyclopentane-1-carboxylic acid;

N-[2-(2'-(tetrazol-5-yl)-phenyl)-naphthalen-6-ylmethyl]-N-propoxycarbonyl-2-aminomethyl-2-ethylbutyric acid;

N-[2-(2'-(tetrazol-5-yl)-phenyl)-naphthalen-6-ylmethyl]-N-propoxycarbonyl-1-aminomethylcyclohexane-1-carboxylic acid;

N-[2-(2'-(tetrazol-5-yl)-phenyl)-naphthalen-6-ylmethyl]-N-ethoxycarbonylvaline;

N-[2-(2'-(tetrazol-5-yl)-phenyl)-naphthalen-6-ylmethyl]-N-ethoxycarbonyl-1-aminomethylcyclopentane-1-carboxylic acid;

N-[2-(2'-(tetrazol-5-yl)-phenyl)-naphthalen-6-ylmethyl]-N-ethoxycarbonyl-2-aminomethyl-2-ethylbutyric acid;

N-[2-(2'-(tetrazol-5-yl)-phenyl)-naphthalen-6-ylmethyl]-N-ethoxycarbonyl-1-aminomethylcyclohexane-1-carboxylic acid;

N-[2-(2'-(tetrazol-5-yl)-phenyl)-quinolin-6-ylmethyl]-N-propoxycarbonylvaline;

N-[2-(2'-(tetrazol-5-yl)-phenyl)-quinolin-6-ylmethyl]-N-propoxycarbonyl-1-aminomethylcyclopentane-1-carboxylic acid;

N-[2-(2'-(tetrazol-5-yl)-phenyl)-quinolin-6-ylmethyl]-N-propoxycarbonyl-2-aminomethyl-2-ethylbutyric acid;

N-[2-(2'-(tetrazol-5-yl)-phenyl)-quinolin-6-ylmethyl]-N-ethoxycarbonyl-1-aminomethylcyclohexane-1-carboxylic acid;

N-[2-(2'-(tetrazol-5-yl)-phenyl)-quinolin-6-ylmethyl]-N-ethoxycarbonyl-[2-(2'-(tetrazol-5-yl)-phenyl)-quinolin-6-ylmethyl]-N-ethoxycarbonylvaline;

N-[2-(2'-(tetrazol-5-yl)-phenyl)-quinolin-6-ylmethyl]-N-ethoxycarbonyl-[2-(2'-(tetrazol-5-yl)-phenyl)-quinolin-6-ylmethyl]-N-ethoxycarbonyl-1-aminomethylcyclopentane-1-carboxylic acid;

N-[2-(2'-(tetrazol-5-yl)-phenyl)-quinolin-6-ylmethyl]-N-ethoxycarbonyl-[2-(2'-(tetrazol-5-yl)-phenyl)-quinolin-6-ylmethyl]-N-ethoxycarbonyl-2-aminomethyl-2-ethylbutyric acid;

N-[2-(2'-(tetrazol-5-yl)-phenyl)-quinolin-6-ylmethyl]-N-ethoxycarbonyl-[2-(2'-(tetrazol-5-yl)-phenyl)-quinolin-6-ylmethyl]-N-ethoxycarbonyl-1-aminomethylcyclohexane-1-carboxylic acid;

N-[2-(2'-(tetrazol-5-yl)-phenyl)-quinolin-6-ylmethyl]-N-valeroyl-1-aminomethylcyclohexane-1-carboxylic acid;

N-[2-(2'-(tetrazol-5-yl)-phenyl)-quinolin-6-ylmethyl]-N--valeroyl-1-aminocyclohexane-1-carboxylic acid;

N-[2-(2'-(tetrazol-5-yl)-phenyl)-quinolin-6-ylmethyl]-N-valeroyl-1-aminocyclopentane-1-carboxylic acid;

N-[2-(2'-(tetrazol-5-yl)-phenyl)-quinolin-6-ylmethyl]-N-butyryl-1-aminomethylcyclopentane- 1-carboxylic acid;

N-[2-(2'-carboxyphenyl)-naphthalen-6-ylmethyl]-N-valeroylvaline;

N-[2-(2'-(tetrazol-5-yl)-phenyl)-naphthalen-6-ylmethyl]-N-butyrylvaline;

N-[2-(2'-carboxyphenyl)-naphthalen-6-ylmethyl]-N-butyryl-valine;

EXAMPLE 14

A solution of 1.675 g of N-[2-(2'-cyanophenyl)-naphthalen-6-ylmethyl]-N-valeroyl-1-aminomethylcyclopentane-1-carboxylic acid ethyl ester and 1.46 g of tributyltin azide in 36 ml of xylene are heated under reflux for 23 hours. The cooled solution is stirred for 1 hour with 10 ml of 2N potassium hydroxide solution. The aqueous phase is extracted with 40 ml of ether, then acidified and extracted three times with 30 ml of CH$_2$Cl$_2$ each time. The oil which separates between the aqueous and the organic phases is collected separately and yields, after chromatography on silica gel 60 (0.040–0.063 mm) using CH$_2$Cl$_2$/CH$_2$OH (9:1) as eluant, N-[2-(2'-(1H-tetrazol-5-yl)-phenyl)-naphthalen-6-ylmethyl]-N-valeroyl-1-aminomethylcyclopentane-1-carboxylic acid ethyl ester, R$_f$=0.31 (CH$_2$Cl$_2$/CH$_3$OH (9:1)).

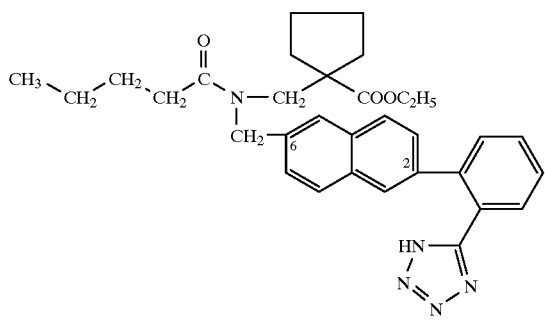

The starting material can be prepared, for example, as follows:

a) A solution of 4,5-dihydro-2-(2-methoxyphenyl)-4,4-dimethyloxazole (I. A. Meyers, M. A. Hanagan & A. L. Mazzu, Heterocycles 15, 361 (1981)) in 400 ml of tetrahydrofuran is added dropwise at 15° to a Grignard solution prepared from 4.69 g of magnesium and 42.59 g of 2-bromo-6-methylnaphthalene (R. G. Jones et al., J.Amer.Chem.Soc. 70, 2843 (1948)) in 420 ml of tetrahydrofuran. After stirring for 4 hours at room temperature, the batch is poured onto a solution of 60 g of ammonium chloride in 1500 ml of water and extracted three times with 500 ml of ether each time. The combined ether phase is dried over MgSO$_4$ and freed of the solution in vacuo. Recrystallisation from hot cyclohexane yields 4,5-dihydro-2-[2-(6'-methylnaphth-2'-yl)-phenyl]-4,4-dimethyloxazole, m.p. 153–155°.

b) A mixture of 63.8 g of 4,5-dihydro-2-[2-(6'-methynaphth-2'-yl)-phenyl]-4,4-dimethyloxazole, 44.3 g of phosphorus oxychloride and 22.8 g of pyridine in 650 ml of toluene is heated under reflux for 2.5 hours. The reaction mixture is cooled to 0°, Na$_2$CO$_3$ solution is added (pH=8) and the batch is then extracted three times with 500 ml of ethyl acetate each time. The ethyl acetate phases are washed three times with 100 ml of water each time, dried over MgSO$_4$ and freed of the solvent in vacuo. The crude product so obtained yields, after chromatography on silica gel 60 (0.040–0.063 mm) using hexane/CH$_2$Cl$_2$/ethyl acetate (9:1:1) as eluant, 6-methyl-2-(2'-cyanophenyl)-naphthalene, m.p. 100–104°.

c) A mixture of 6.30 g of 6-methyl-2-(2'-cyanophenyl)-naphthalene, 4.60 g of N-bromosuccinimide and 0.085 g of azoisobutyronitrile in 70 ml of carbon tetrachloride is heated at 110° for 4 hours. The cooled reaction mixture is extracted twice with 45 ml of 2N sodium hydroxide solution each time. The aqueous phases are then extracted with 50 ml of CH$_2$Cl in each case. The combined organic phases are dried over MgSO$_4$. After removing the solvent in vacuo, the crude product is recrystallised from toluene/hexane and yields 6-bromomethyl-2-(2'-cyanophenyl)-naphthalene, m.p. 171–172°.

d) A solution of 1.290 g of 6-bromomethyl-2-(2'-cyanophenyl)-naphthalene, 0.694 g of 1-aminomethylcyclopentane-1-carboxylic acid ethyl ester and 0.71 ml of N,N-diisopropyl-N-ethylamine in 10 ml of toluene is heated at 80° for 3 hours. The filtrate is diluted with 20 ml of ether and extracted three times with 10 ml of water each time. The organic phase, after drying over Na$_2$SO$_4$ and removing the solvents in vacuo, yields a viscous oil. The resulting crude product yields, after chromatography on silica gel 60 (0.040–0.063 mm) using CH$_2$Cl$_2$/CH$_3$OH (98:2) as eluant, N-2-(2'-cyanophenyl)-naphthalen-6-ylmethyl)-1-aminomethylcyclopentane-1-carboxylic acid ethyl ester, R$_f$=0.33 (CH$_2$Cl$_2$/CH$_3$OH (95:5)).

e) A solution of 1.40 g of N-[2-(2'-cyanophenyl)-naphthalen-6-ylmethyl]-1-aminomethylcyclopentane-1-carboxylic acid ethyl ester, 0.49 ml of triethylamine and 0.41 ml of valeroyl chloride in 14 ml of CH$_2$Cl$_2$ is stirred at room temperature for 2.5 hours, then diluted with 50 ml of ether and washed in succession with 7 ml of 1N potassium hydroxide solution, 5 ml of 1N hydrochloric acid, 5 ml of saturated NaHCO$_3$ solution and twice with 5 ml of water each time. The organic phase is dried over Na$_2$SO$_4$ and is freed of the solvents in vacuo to yield pure N-[2-(2'-cyanophenyl)-naphthalen-6-ylmethyl]-N-valeroyl-1-aminomethylcyclopentane-1-carboxylic acid ethyl ester, R$_f$=0.69 (CH$_2$Cl$_2$/CH$_3$OH (95:5)).

EXAMPLE 15

A mixture of 0.888 g of N-[2-(2'-(1H-tetrazol-5-yl)-phenyl)-naphthalen-6-ylmethyl]-N-valeroyl-1-aminomethylcyclopentane-1-carboxylic acid ethyl ester, 8 ml of ethanol and 5 ml of 2N potassium hydroxide solution is heated under reflux for 2.5 hours. The cooled reaction solution is neutralised and concentrated by evaporation in vacuo. The residue is taken up in 30 ml of CH$_2$Cl$_2$ and extracted with 5 ml of 1N potassium hydroxide solution. The alkaline phase is adjusted to pH=1 using 3 ml of 4N hydrochloric acid and extracted three times with 25 ml of CH$_2$Cl$_2$ each time. Drying the CH$_2$Cl$_2$ phases over Na$_2$SO$_4$ and removing the solvent in vacuo yields N-[2-(2'-(1H-tetrazol-5-yl)-phenyl-naphthalen-6-ylmethyl]-N-valeroyl-1-aminomethylcyclopentane-1-carboxylic acid, R$_f$=0.21 (CH$_2$Cl$_2$/CH$_3$OH (9:1)).

EXAMPLE 16

A solution of 2.30 g of N-[2-(2'-cyanophenyl)-6-ylmethylnaphthalene]-N-valeroyl-3-amino-2,2-dimethylpropionic acid ethyl ester and 2.16 g of tributyltin azide in 50 ml of xylene is heated under reflux for 16 hours. The cooled solution is stirred with 50 ml of 2N potassium hydroxide solution for 30 minutes. The aqueous phase is separated off, acidified with 30 ml of 4N hydrochloric acid and extracted twice with 25 ml of CH$_2$Cl$_2$ each time. After drying over Na$_2$SO$_4$ and removing the solvent in vacuo, the residue is dissolved in 25 ml of ethanol, mixed with 10 ml of 2N potassium hydroxide solution and heated under reflux for 3 hours. The cooled reaction mixture is rendered acidic with 8 ml of 4N hydrochloric acid and concentrated by evaporation in vacuo and yields, after chromatography on silica gel 60 (0.040–0.063 mm) using CH$_2$Cl$_2$/CH$_3$OH (9:1) as eluant, N-[2-(2'-(1H-tetrazol-5-yl)-phenylnaphthalen-6-ylmethyl]-N-valeroyl-3-amino-2,2-dimethylpropionic acid, R$_f$=0.55 (CH$_2$Cl$_2$/CH$_3$OH (4:1)).

The starting material can be prepared, for example, as follows:

a) A mixture of 1.82 g of 3-amino-2,2-dimethylpropionic acid ethyl ester and 1.61 g of 6-bromomethyl-2-(2'- cyanophenyl)-naphthalene is heated at 100° for 15 minutes and then taken up in 100 ml of ethyl acetate which is extracted with 50 ml of 1N hydrochloric acid and 50 ml of saturated NaHCO₃ solution. The organic phase yields, after drying over Na₂SO₄ and removing the solvent in vacuo, N-[2-(2'-cyanophenyl)-naphthalen-6-ylmethyl]-3-amino-2,2-dimethylpropionic acid ethyl ester, R_f=0.45 (CH₂Cl₂/CH₃OH (95:5)).

b) A solution of 1.90 g of N-[2-(2'-cyanophenyl)-naphthalen-6-ylmethyl]-3-amino-2,2-dimethylpropionic acid ethyl ester, 1.32 ml of N,N-diisopropyl-N-ethylamine and 0.72 ml of valeroyl chloride in 50 ml of toluene is stirred at room temperature for 1 hour. The reaction mixture is washed in succession with 2×25 ml of 1N hydrochloric acid, 25 ml of water, 25 ml of saturated NaHCO₃ solution and 25 ml of brine. The organic phase yields, after drying over Na₂SO₄ and removing the solvent in vacuo, N-[2-(2'-cyanophenyl)-naphthalen-6-ylmethyl]-N-valeroyl-3-amino-2,2-dimethylpropionic acid ethyl ester R_f=0.35 (CH₂Cl₂/CH₃OH (95:5)).

EXAMPLE 17

A solution of 1.6 g of N-[2-(2'-(1H-tetrazol-5-yl)-phenyl)-naphthalen)-6-ylmethyl]-N-butyrylvaline benzyl ester in 30 ml of 2N NaOH and 50 ml of methanol is heated under reflux for 0.5 hour. The cooled solution is filtered so that is free of fibres and the methanol is removed using a rotary evaporator. After acidifying with HCl, the N-[2-(2'-(1H-tetrazol-5-yl)-phenyl)-naphthalene)-6-ylmethyl]-N-butyrylvaline having a water content of approximately 2.5% crystallises in the form of colourless crystals. M.p.: 115–125°; R_f=0.16 (CH₂Cl₂/ethanol (9:1)).

The starting material can be prepared, for example, as follows:

a) A solution of 6.58 g of valine benzyl ester toluenesulfonic acid salt, 5.9 ml of Hünig base and 2.8 g of 6-bromomethyl-2-(2'-cyanophenyl)-naphthalene in 30 ml of N,N-dimethylformamide is heated at 80° for 2 hours. The cooled reaction solution is poured out onto 100 ml of 1% NaHCO₃ solution and the product is extracted with 3×100 ml of ethyl acetate. The organic phases are washed with 3×50 ml of water, combined, dried over magnesium sulfate, filtered and concentrated by evaporation. The crude product of 5.8 g is chromatographed on silica gel 60 (0.04–0.063 mm) using hexane/ethyl acetate (4:1) as eluant. N-[2-(2'-cyanophenyl)-naphthalen-6-ylmethyl]-valine benzyl ester is obtained in the form of a yellow oil. R_f=0.3 (hexane/ethyl acetate (4:1)).

b) A solution of 1.95 g of N-[2-(2'-cyanophenyl)-naphthalen-6-ylmethyl]-N-butyrylvaline benzyl ester, 1.1 ml of Hünig base and 0.55 g of butyric acid chloride in 20 ml of ethyl acetate is stirred at room temperature for 18 hours. The batch is diluted with 50 ml of ethyl acetate, washed once with 25 ml of 2N soda solution and twice with 25 ml of water each time. The aqueous phases are re-extracted twice with 50 ml of ethyl acetate each time. The organic phases yield, after drying and concentrating by evaporation, N-[-2-(2'-cyanophenyl)-naphthalen-6-ylmethyl]-N-butyrylvaline benzyl ester in the form of a thick yellow oil. R_f=0.2 (hexane/ethyl acetate (4:1)).

c) A solution of N-[2-(2'-cyanophenyl)-naphthalen-6-ylmethyl]-N-butyrylvaline benzyl ester and 2g of tributyltin azide in 10 ml of a mixture of xylene isomers is boiled under reflux for 24 hours. After cooling to room temperature, 5 ml of 5N HCl in ether are added and the batch is stirred at room temperature for 0.5 hour. 80 ml of cyclohexane are added and the supernatant solution is then decanted. The residue is triturated twice more with 50 ml of cyclohexane each time and the supernatant solution is decanted off and discarded. The residue is chromatographed on silica gel 60 to yield N-[2-(2'-(1H-tetrazol-5-yl)-phenyl)-naphthalen)-6-ylmethyl]-N-butyrylvaline benzyl ester in the form of a yellow foam: R_f=0.32 (CH₂Cl₂/ethanol (95:5)).

EXAMPLE 18

Analogously to Example 17, there is obtained from N-[2-(2'-(1H-tetrazol-5-yl)-phenyl)-naphthalen)-6-ylmethyl]-N-valeroylvaline benzyl ester by hydrolysis with NaOH/methanol and subsequent working-up. N-[2-(2'-(1H-tetrazol-5-yl)-phenyl)-naphthalen)-6-ylmethyl]-N-valeroylvaline having a water content of 2.5%. M.p.: 118–127°; R_f=0.37 (CH₂Cl₂/ethanol (9:1)).

EXAMPLE 19

In an analogous manner, for example as described in one of the above Examples, or starting from one of the products described above, it is possible to prepare:

N-[2-(2'-(1H-tetrazol-5-yl)-phenyl)-naphthalen-6-ylmethyl]-N-valeroyl-1-aminomethyl-1-hydroxymethylcyclopentane;

N-[2-(2'-(1H-tetrazol-5-yl)-phenyl)-naphthalen-6-ylmethyl]-N-valeroyl-1-aminomethyl-1-formylcyclopentane;

N-[2-(2'-(1H-tetrazol-5-yl)-phenyl)-quinolin-6-ylmethyl]-N-valeroyl-1-aminomethyl-1-hydroxymethylcyclopentane;

N-[2-(2'-(1H-tetrazol-5-yl)-phenyl)-quinolin-6-ylmethyl]-N-valeroyl-1-aminomethyl-1-formylcyclopentane;

N-[2-(2'-(1H-tetrazol-5-yl)-phenyl)-naphthalen-6-ylmethyl]-N-valeroyl-N-1-hydroxymethylisobutane;

N-[2-(2'-(1H-tetrazol-5-yl)-phenyl)-naphthalen-6-ylmethyl]-N-valeroyl-N-1-formylisobutane;

N-[2-(2'-(1H-tetrazol-5-yl)-phenyl)-quinolin-6-ylmethyl]-N-valeroyl-N-1-hydroxymethylisobutane;

N-[2-(2'-(1H-tetrazol-5-yl)-phenyl)-quinolin-6-ylmethyl]-N-valeroyl-N-1-formylisobutane;

EXAMPLE 20

A solution of 2.93 g of N-[3-bromo-2-[2'-(1-trityltetrazol-5-yl)-phenyl]-benzofuran-5-ylmethyl]-N-valeroyl-1-aminomethylcyclopentane-1-carboxylic acid ethyl ester and 0.5 ml of concentrated hydrochloric acid in 50 ml of methanol is stirred at room temperature for 1.5 hours. The cooled solution is rendered alkaline with 10 ml of 2N sodium hydroxide solution and concentrated by evaporation. The residue is taken up in 50 ml of water and extracted with 100 ml of ether. The aqueous phase is acidified with 15 ml of 2N hydrochloric acid and extracted with 100 ml and 50 ml of ethyl acetate. The ethyl acetate phases yield, after washing with 50 ml of water and 50 ml of brine and removing the solvent in vacuo, N-[3-bromo-2-[2'-(1H-tetrazol-5-yl)-phenyl]-benzofuran-5-ylmethyl]-N-valeroyl-1-aminomethylcyclopentane-1-carboxylic acid ethyl ester R_f=0.52 (CH₂Cl₂/CH₃OH (4:1)).

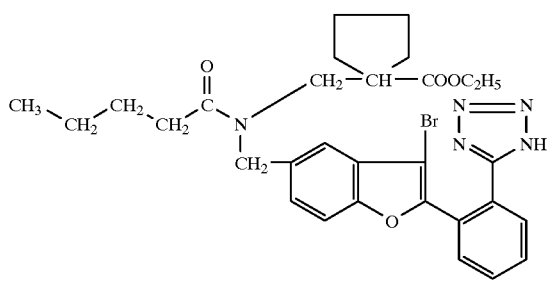

In an analogous manner, it is possible to obtain:

N-[3-bromo-2-[2'-(1H-tetrazol-5-yl)-phenyl]-benzofuran-5-ylmethyl]-N-butyryl-1-aminomethylcyclopentane-1-carboxylic acid ethyl ester;

N-[3-bromo-2-[2'-(1H-tetrazol-5-yl)-phenyl]-benzofuran-5-ylmethyl]-N-caproyl-1-aminomethylcyclopentane-1-carboxylic acid ethyl ester;

N-[3-bromo-2-[2'-(1H-tetrazol-5-yl)-phenyl]-benzofuran-5-ylmethyl]-N-valeroylvaline ethyl ester;

N-[3-bromo-2-[2'-(1H-tetrazol-5-yl)-phenyl]-benzofuran-5-ylmethyl]-N-butyrylvaline ethyl ester;

N-[3-bromo-2-[2'-(1H-tetrazol-5-yl)-phenyl]-benzofuran-5-ylmethyl]-N-caproylvaline ethyl ester;

N-[3-bromo-2-[2'-(1H-tetrazol-5-yl)-phenyl]-benzofuran-5-ylmethyl]-N-valeroylalanine ethyl ester;

The starting material can be prepared, for example, as follows:

a) A mixture of 23.3 g of 2-(2'-cyanophenyl)-5-methylbenzofuran and 67 g of tributyltin azide is slowly heated to 160° and then maintained at that temperature for 3 hours. The cooled solution is taken up in 600 ml of 1N sodium hydroxide solution and extracted five times with 200 ml of ether each time. The product is precipitated from the aqueous phase by introducing 4N hydrochloric acid dropwise (to pH=1). By filtering with suction and drying the precipitate at 70° in vacuo, 2-[2'-(1H-tetrazol-5-yl)-phenyl]-5-methylbenzofuran, $R_f$=0.51 ($CH_2Cl_2/CH_3OH$ (4:1)) is obtained.

b) A solution of 11.6 g of bromine in 28 ml of carbon tetrachloride is added dropwise over the course of 35 minutes to a suspension of 10.0 g of 2-[2'-(1H-tetrazol-5-yl)-phenyl]-5-methylbenzofuran in 418 ml of dioxane. After stirring for 3 hours at room temperature, 12.6 ml of cyclohexene are added dropwise and then the reaction mixture is concentrated by evaporation in vacuo. The residue is taken up in 50 ml of 2N sodium hydroxide solution and extracted with 100 ml of ether. Three clear phases form. The two lower phases are separated off, acidified with 40 ml of 4N hydrochloric acid and extracted three times with 100 ml of ethyl acetate each time. The combined ethyl acetate phases are washed with 100 ml of brine and, after removal of the solvent in vacuo, they result in a yellow oil which yields crystalline 3-bromo-2-[2'-(1H-tetrazol-5-yl)-phenyl]-5-methylbenzofuran, m.p. 167–168°, from toluene.

c) 5.89 g of triethylamine, 8.14 g of triphenylchloromethane and 0.10 g of 4-N,N-dimethylaminopyridine are added in succession to a suspension of 10.37 g of 3-bromo-2-[2'-(1H-tetrazol-5-yl)-phenyl]-5-methylbenzofuran in 300 ml of $CH_2Cl_2$ and the batch is stirred for 3 hours at room temperature. The reaction solution is washed with 150 ml of water and 150 ml of brine, concentrated in vacuo to a volume of 50 ml and chromatographed on silica gel 60 (40–63 μm) using $CH_2Cl_2$ as eluant. The product, of $R_f$=0.82 ($CH_2Cl_2/CH_3OH$ (95:5)), yields crystalline 3-bromo-2-[2-(1-trityltetrazol-5-yl)-phenyl]-5-methylbenzofuran, m.p. 199–200°, from ether.

d) 4.48 g of N-bromosuccinimide and 0.22 g of dibenzoyl peroxide are added to a solution, heated to 50°, of 15.0 g of 3-bromo-2-[2'-(1-trityltetrazol-5-yl)-phenyl]-5-methylbenzofuran in 415 ml of carbon tetrachloride. The mixture is heated under reflux for 3.5 hours. The reaction mixture is cooled to 5° and filtered. The filtrate, after being washed with 100 ml of water and 100 ml of brine, dried over $Na_2SO_4$, concentrated by evaporation in vacuo and taken up in ether/$CH_3OH$ (1:1), yields crystalline 3-bromo-5-bromomethyl-2-[2'-(1-trityltetrazol-5-yl)-phenyl]-5-methylbenzofuran, m.p. 192–193°.

e) A solution of 2.03 g of 3-bromo-5-bromomethyl-2-[2'-(1-trityltetrazol-5-yl)-phenyl]-5-methylbenzofuran and 1.28 g of 1-aminomethylcyclopentane-1-carboxylic acid ethyl ester in 25 ml of toluene is heated at 100° for one hour. The reaction solution is diluted with 25 ml of toluene and washed in succession with 25 ml of 1N hydrochloric acid, 25 ml of water and 25 ml of brine and, after removal of the solvent in vacuo, yields N-[3-bromo-2-[2'-(1trityltetrazol-5-yl)-phenyl]-benzofuran-5-ylmethyl]-1-aminomethylcyclopentane-1-carboxylic acid ethyl ester, $R_f$=0.84 ($CH_2Cl_2/CH_3OH$ (4:1)).

f) A solution of 2.51 g of N-[3-bromo-2-[2'-(1-trityltetrazol-5-yl)-phenyl]-benzofuran-5-ylmethyl]-1-aminomethylcyclopentane-1-carboxylic acid ethyl ester, 0.79 ml of ethyldiisopropylamine and 0.43 ml of valeroyl chloride in 50 ml of toluene is stirred at room temperature for one hour. The reaction mixture is diluted with 50 ml of toluene and washed in succession with 25 ml of 1N hydrochloric acid (twice), 25 ml of water, 25 ml of saturated $NaHCO_3$ solution and 25 ml of brine. The aqueous phases are re-extracted with 50 ml of toluene. After removing the solvent in vacuo, the combined organic phases yield N-[3-bromo-2-[2'-(1-trityltetrazol-5-yl)-phenyl]-benzofuran-5-ylmethyl]-N-valeroyl-1-aminomethylcyclopentane-1-carboxylic acid ethyl ester, $R_f$=0.23 ($CH_2Cl_2/CH_3OH$ (99:1)).

EXAMPLE 21

A solution of 0.913 g of N-[3-bromo-2-[2'-(1H-tetrazol-5-yl)-phenyl]-benzofuran-5-ylmethyl]-N-valeroyl-1-aminomethylcyclopentane-1-carboxylic acid ethyl ester and 10 ml of 2N sodium hydroxide solution in 15 ml of ethanol is heated at 100° for 3 hours. The cooled solution is acidified with 8 ml of 4N hydrochloric acid and concentrated by evaporation in vacuo. The residue yields, after chromatography on silica gel 60 (40–63 μm) using $CH_2Cl_2/CH_3OH$ (95:5) as eluant, pure N-[3-bromo-2-[2'-(1H-tetrazol-5-yl)-phenyl]-benzofuran-5-ylmethyl]-N-valeroyl-1-aminomethylcyclopentane-1-carboxylic acid, $R_f$=0.43 ($CH_2Cl_2/CH_3OH$ (4:1)).

In an analogous manner it is possible to prepare:

N-[3-bromo-2-[2'-(1H-tetrazol-5-yl)-phenyl]-benzofuran-5-ylmethyl]-N-butyryl-1-aminomethylcyclopentane-1-carboxylic acid;

N-[3-bromo-2-[2'-(1H-tetrazol-5-yl)-phenyl]-benzofuran-5-ylmethyl]-N-caproyl-1-aminomethylcyclopentane-1-carboxylic acid;

N-[3-bromo-2-[2'-(1H-tetrazol-5-yl)-phenyl]-benzofuran-5-ylmethyl]-N-valeroylvaline;

N-[3-bromo-2-[2'-(1H-tetrazol-5-yl)-phenyl]-benzofuran-5-ylmethyl]-N-butyrylvaline;

N-[3-bromo-2-[2'-(1H-tetrazol-5-yl)-phenyl]-benzofuran-5-ylmethyl]-N-caproylvaline;

N-[3-bromo-2-[2'-(1H-tetrazol-5-yl)-phenyl]-benzofuran-5-ylmethyl]-N-valeroylalanine.

EXAMPLE 22

0.4 g of N-[2-(2'-(1H-tetrazol-5-yl)-phenyl)-naphthalen-6-ylmethyl]-N-valeroylvaline methyl ester is heated in an autoclave for 17 hours at 100° together with 20 ml of a solution of methylamine in ethanol (33%). The reaction mixture is then concentrated to dryness by evaporation using a rotary evaporator. The residue is shaken with 50 ml of ethyl acetate and 10 ml of 2N HCl in a separating funnel. The aqueous phase is separated off and extracted twice with 20 ml of ethyl acetate each time. The organic phases are washed twice with 10 ml of water each time, combined and dried over magnesium sulfate. After filtering and concentrating the filtrate by evaporation, the residue is chromatographed over silica gel 60 to yield N-[2-(2'-(1H-tetrazol-5-yl)-phenyl)-naphthalen-6-ylmethyl]-N-valeroylvaline methylamide in the form of a pale yellow resin. $R_f$=0.14 ($CH_2Cl_2$/ethanol 95/5).

The starting material can be prepared, for example, as follows:

a) A solution of 3.39 g of valine methyl ester hydrochloride, 9.1 ml of Hünig base and 5.42 g of 6-bromomethyl-2-(2'-cyanophenyl)-naphthalene in 50 ml of N,N-dimethylformamide is heated at 80° for 3 hours. The cooled reaction solution is poured out onto 200 ml of 1% $NaHCO_3$ solution and the product is extracted three times with 200 ml of ethyl acetate each time. The organic phases are washed 3 times with 100 ml of water each time, combined, dried over magnesium sulfate, filtered and concentrated by evaporation. The crude product of 6.8 g is chromatographed on silica gel 60 to yield N-[2-(2'-cyanophenyl)-naphthalen-6-ylmethyl]-valine methyl ester in the form of an orange oil. $R_f$=0.24 (hexane/ethyl acetate: 4:1).

b) A solution of 4.94 g of N-[2-(2'-cyanophenyl)-naphthalen-6-ylmethyl]-valine methyl ester, 3.4 ml of Hünig base and 1.29 g of valeric acid chloride in 50 ml of ethyl acetate is stirred at room temperature for 18 hours. The batch is diluted with 150 ml of ethyl acetate, washed once with 40 ml of 2N soda solution and twice with 50 ml of water each time. The aqueous phases are re-extracted twice with 100 ml of ethyl acetate each time. The organic phases yield, after drying and concentrating by evaporation, N-[2-(2'-cyanophenyl)-naphthalen-6-ylmethyl]-N-valeroylvaline methyl ester in the form of an orange oil. $R_f$=0.18 (hexane/ethyl acetate 4:1).

c) A solution of 6.68 g of N-[2-(2'-cyanophenyl)-naphthalen-6-ylmethyl]-N-valeroylvaline methyl ester and 6.8 g of tributyltin azide in 40 ml of a mixture of xylene isomers is boiled under reflux for 48 hours. After cooling to room temperature, 5 ml of 5N HCl in ether are added and the batch is stirred for half an hour at room temperature. 150 ml of cyclohexane are added and then the supernatant solution is decanted from the precipitated resinous residue. The residue is triturated twice more with 150 ml of cyclohexane each time and the supernatant solution is decanted off and discarded. The residue is finally chromatographed on silica gel 60 to yield N-[2-(2'-(1H-tetrazol-5-yl)-phenyl)-naphthalen-6-ylmethyl]-N-valeroylvaline methyl ester in the form of a yellow foam. $R_f$=0.30 ($CH_2Cl_2$/ethanol 95/5).

EXAMPLE 23

In an analogous manner, for example as described in one of Examples 1–22, it is possible to prepare:

N-{3-bromo-2-[2'-(1H-tetrazol-5-yl)-phenyl]-benzofuran-5-ylmethyl}-N-butyryl-1-aminomethylcyclopentane-1-carboxylic acid;

N-{3-bromo-2-[2'-(1H-tetrazol-5-yl)-phenyl]-benzofuran-5-ylmethyl}-N-caproyl-1-aminomethylcyclopentane-1-carboxylic acid;

N-{3-bromo-2-[2'-(1H-tetrazol-5-yl)-phenyl]-benzofuran-5-ylmethyl}-N-propionyl-1-aminomethylcyclopentane-1-carboxylic acid;

N-{3-bromo-2-[2'-(1H-tetrazol-5-yl)-phenyl]-benzofuran-5-ylmethyl}-N-ethoxycarbonyl-1-aminomethylcyclopentane-1-carboxylic acid;

N-{3-bromo-2-[2'-(1H-tetrazol-5-yl)-phenyl]-benzofuran-5-ylmethyl}-N-propoxycarbonyl-1-aminomethylcyclopentane-1-carboxylic acid;

N-{3-bromo-2-[2'-(1H-tetrazol-5-yl)-phenyl]-benzofuran-5-ylmethyl}-N-cyclopropoxycarbonyl-1-aminomethylcyclopentane-1-carboxylic acid;

N-{3-bromo-2-[2'-(1H-tetrazol-5-yl)-phenyl]-benzofuran-5-ylmethyl}-N-cyclopentylcarbonyl-1-aminomethylcyclopentane-1-carboxylic acid;

N-{3-bromo-2-[2'-(1H-tetrazol-5-yl)-phenyl]-benzofuran-5-ylmethyl}-N-cyclopropylcarbonyl-1-aminomethylcyclopentane-1-carboxylic acid;

N-{3-bromo-2-[2'-(1H-tetrazol-5-yl)-phenyl]-benzofuran-5-ylmethyl}-N-cyclopropylmethylcarbonyl-1-aminomethylcyclopentane-1-carboxylic acid;

N-{3-bromo-2-[2'-(1H-tetrazol-5-yl)-phenyl]-benzothiophen-5-ylmethyl}-N-butyryl-1-aminomethylcyclopentane-1-carboxylic acid;

N-{3-bromo-2-[2'-(1H-tetrazol-5-yl)-phenyl]-benzothiophen-5-ylmethyl}-N-caproyl-1-aminomethylcyclopentane-1-carboxylic acid;

N-{3-bromo-2-[2'-(1H-tetrazol-5-yl)-phenyl]-benzothiophen-5-ylmethyl}-N-propionyl-1-aminomethylcyclopentane-1-carboxylic acid;

N-{3-bromo-2-[2'-(1H-tetrazol-5-yl)-phenyl]-benzothiophen-5-ylmethyl}-N-ethoxycarbonyl-1-aminomethylcyclopentane-1-carboxylic acid;

N-{3-bromo-2-[2'-(1H-tetrazol-5-yl)-phenyl]-benzothiophen-5-ylmethyl}-N-propoxycarbonyl-1-aminomethylcyclopentane-1-carboxylic acid;

N-{3-bromo-2-[2'-(1H-tetrazol-5-yl)-phenyl]-benzothiophen-5-ylmethyl}-N-cyclopropoxycarbonyl-1-aminomethylcyclopentane-1-carboxylic acid;

N-{3-bromo-2-[2'-(1H-tetrazol-5-yl)-phenyl]-benzothiophen-5-ylmethyl}-N-cyclopentylcarbonyl-1-aminomethylcyclopentane-1-carboxylic acid;

N-{3-bromo-2-[2'-(1H-tetrazol-5-yl)-phenyl]-benzothiophen-5-ylmethyl}-N-cyclopropylcarbonyl-1-aminomethylcyclopentane-1-carboxylic acid;

N-{3-bromo-2-[2'-(1H-tetrazol-5-yl)-phenyl]-benzothiophen-5-ylmethyl}-N-cyclopropylmethylcarbonyl-1-aminomethylcyclopentane-1-carboxylic acid;

N-{3-bromo-2-[2'-(1H-tetrazol-5-yl)-phenyl]-indol-5-ylmethyl}-N-butyryl-1-aminomethylcyclopentane-1-carboxylic acid;

N-{3-bromo-2-[2'-(1H-tetrazol-5-yl)-phenyl]-indol-5-ylmethyl}-N-caproyl-1-aminomethylcyclopentane-1-carboxylic acid;

N-{3-bromo-2-[2'-(1H-tetrazol-5-yl)-phenyl]-indol-5-ylmethyl}-N-propionyl-1-aminomethylcyclopentane-1-carboxylic acid;

N-{3-bromo-2-[2'-(1H-tetrazol-5-yl)-phenyl]-indol-5-ylmethyl}-N-ethoxycarbonyl-1-aminomethylcyclopentane-1-carboxylic acid;

N-{3-bromo-2-[2'-(1H-tetrazol-5-yl)-phenyl]-indol-5-ylmethyl}-N-propoxycarbonyl-1-aminomethylcyclopentane-1-carboxylic acid;

N-{3-bromo-2-[2'-(1H-tetrazol-5-yl)-phenyl]-indol-5-ylmethyl}-N-cyclopropoxycarbonyl-1-aminomethylcyclopentane-1-carboxylic acid;

N-{3-bromo-2-[2'-(1H-tetrazol-5-yl)-phenyl]-indol-5-ylmethyl}-N-cyclopentylcarbonyl-1-aminomethylcyclopentane-1-carboxylic acid;

N-{3-bromo-2-[2'-(1H-tetrazol-5-yl)-phenyl]-indol-5-ylmethyl}-N-cyclopropylcarbonyl-1-aminomethylcyclopentane-1-carboxylic acid;

N-{3-bromo-2-[2'-(1H-tetrazol-5-yl)-phenyl]-indol-5-ylmethyl}-N-cyclopropylmethylcarbonyl-1-aminomethylcyclopentane-1-carboxylic acid;

N-{3-bromo-2-[2'-carboxyphenyl]-benzofuran-5-ylmethyl}-N-butyryl-1-aminomethylcyclopentane-1-carboxylic acid;

N-{3-bromo-2-[2'-carboxyphenyl]-benzofuran-5-ylmethyl}-N-caproyl-1-aminomethylcyclopentane-1-carboxylic acid;

N-{3-bromo-2-[2'-carboxyphenyl]-benzofuran-5-ylmethyl}-N-propionyl-1-aminomethylcyclopentane-1-carboxylic acid;

N-{3-bromo-2-[2'-carboxyphenyl]-benzofuran-5-ylmethyl}-N-ethoxycarbonyl-1-aminomethylcyclopentane-1-carboxylic acid;

N-{3-bromo-2-[2'-carboxyphenyl]-benzofuran-5-ylmethyl}-N-propoxycarbonyl-1-aminomethylcyclopentane-1-carboxylic acid;

N-{3-bromo-2-[2'-carboxyphenyl]-benzofuran-5-ylmethyl}-N-cyclopropoxycarbonyl-1-aminomethylcyclopentane-1-carboxylic acid;

N-{3-bromo-2-[2'-carboxyphenyl]-benzofuran-5-ylmethyl}-N-cyclopentylcarbonyl-1-aminomethylcyclopentane-1-carboxylic acid;

N-{3-bromo-2-[2'-carboxyphenyl]-benzofuran-5-ylmethyl}-N-cyclopropylcarbonyl-1-aminomethylcyclopentane-1-carboxylic acid;

N-{3-bromo-2-[2'-carboxyphenyl]-benzofuran-5-ylmethyl}-N-cyclopropylmethylcarbonyl-1-aminomethylcyclopentane-1-carboxylic acid;

N-{3-bromo-2-[2'-carboxyphenyl]-5-ylmethyl}-N-butyryl-1-aminomethylcyclopentane-1-carboxylic acid;

N-{3-bromo-2-[2'-carboxyphenyl]-5-ylmethyl}-N-caproyl-1-aminomethylcyclopentane-1-carboxylic acid;

N-{3-bromo-2-[2'-carboxyphenyl]-5-ylmethyl}-N-propionyl-1-aminomethylcyclopentane-1-carboxylic acid;

N-{3-bromo-2-[2'-carboxyphenyl]-5-ylmethyl}-N-ethoxycarbonyl-1-aminomethylcyclopentane-1-carboxylic acid;

N-{3-bromo-2-[2'-carboxyphenyl]-5-ylmethyl}-N-propoxycarbonyl-1-aminomethylcyclopentane-1-carboxylic acid;

N-{3-bromo-2-[2'-carboxyphenyl]-5-ylmethyl}-N-cyclopropoxycarbonyl-1-aminomethylcyclopentane-1-carboxylic acid;

N-{3-bromo-2-[2-carboxyphenyl]-5-ylmethylbenzothiophene}-N-cyclopentylcarbonyl-1-aminomethylcyclopentane-1-carboxylic acid;

N-{3-bromo-2-[2-carboxyphenyl]-5-ylmethylbenzothiophene}-N-cyclopropylcarbonyl-1-aminomethylcyclopentane-1-carboxylic acid;

N-{3-bromo-2-[2-carboxyphenyl]-5-ylmethylbenzothiophene}-N-cyclopropylmethylcarbonyl-1-aminomethylcyclopentane-1-carboxylic acid;

N-{3-bromo-2-[2'-carboxyphenyl]-5-ylmethylindole}-N-butyryl-1-aminomethylcyclopentane-1-carboxylic acid;

N-{3-bromo-2-[2'-carboxyphenyl]-5-ylmethylindole}-N-caproyl-1-aminomethylcyclopentane-1-carboxylic acid;

N-{3-bromo-2-[2'-carboxyphenyl]-5-ylmethylindole}-N-propionyl-1-aminomethylcyclopentane-1-carboxylic acid;

N-{3-bromo-2-[2'-carboxyphenyl]-5-ylmethylindole}-N-ethoxycarbonyl-1-aminomethylcyclopentane-1-carboxylic acid;

N-{3-bromo-2-[2'-carboxyphenyl]-5-ylmethylindole}-N-propoxycarbonyl-1-aminomethylcyclopentane-1-carboxylic acid;

N-{3-bromo-2-[2'-carboxyphenyl]-5-ylmethylindole}-N-cyclopropoxycarbonyl-1-aminomethylcyclopentane-1-carboxylic acid;

N-{3-bromo-2-[2'-carboxyphenyl]-5-ylmethylindole}-N-cyclopentylcarbonyl-1-aminomethylcyclopentane-1-carboxylic acid;

N-{3-bromo-2-[2'-carboxyphenyl]-5-ylmethylindole}-N-cyclopropylcarbonyl-1-aminomethylcyclopentane-1-carboxylic acid;

N-{3-bromo-2-[2'-carboxyphenyl]-5-ylmethylindole}-N-cyclopropylmethylcarbonyl-1-aminomethylcyclopentane-1-carboxylic acid;

N-{3-bromo-2-[2'-(1H-tetrazol-5-yl)-phenyl]-5-ylmethylbenzofuran}-N-butyrylvaline;

N-{3-bromo-2-[2'-(1H-tetrazol-5-yl)-phenyl]-5-ylmethylbenzofuran}-N-caproylvaline;

N-{3-bromo-2-[2'-(1H-tetrazol-5-yl)-phenyl]-5-ylmethylbenzofuran}-N-propionylvaline;

N-{3-bromo-2-[2'-(1H-tetrazol-5-yl)-phenyl]-5-ylmethylbenzofuran}-N-ethoxycarbonylvaline;

N-{3-bromo-2-[2'-(1H-tetrazol-5-yl)-phenyl]-5-ylmethylbenzofuran}-N-propoxycarbonylvaline;

N-{3-bromo-2-[2'-(1H-tetrazol-5-yl)-phenyl]-5-ylmethylbenzofuran}-N-cyclopropoxycarbonylvaline;

N-{3-bromo-2-[2'-(1H-tetrazol-5-yl)-phenyl]-5-ylmethylbenzofuran}-N-cyclopentylcarbonylvaline;

N-{3-bromo-2-[2'-(1H-tetrazol-5-yl)-phenyl]-5-ylmethylbenzofuran}-N-cyclopropylcarbonylvaline;

N-{3-bromo-2-[2'-(1H-tetrazol-5-yl)-phenyl]-5-ylmethylbenzofuran}-N-cyclopropylmethylcarbonylvaline;

N-{3-bromo-2-[2'-(1H-tetrazol-5-yl)-phenyl]-5-ylmethylbenzothiophene}-N-butyrylvaline;

N-{3-bromo-2-[2'-(1H-tetrazol-5-yl)-phenyl]-5-ylmethylbenzothiophene}-N-caproylvaline;

N-{3-bromo-2-[2'-(1H-tetrazol-5-yl)-phenyl]-5-ylmethylbenzothiophene}-N-propionylvaline;

N-{3-bromo-2-[2'-(1H-tetrazol-5-yl)-phenyl]-5-ylmethylbenzothiophene}-N-ethoxycarbonylvaline;

N-{3-bromo-2-[2'-(1H-tetrazol-5-yl)-phenyl]-5-ylmethylbenzothiophene}N-propoxycarbonylvaline;

N-{3-bromo-2-[2'-(1H-tetrazol-5-yl)-phenyl]-5-ylmethylbenzothiophene}-N-cyclopropoxycarbonylvaline;

N-{3-bromo-2-[2'-(1H-tetrazol-5-yl)-phenyl]-5-ylmethylbenzothiophene}-N-cyclopentylcarbonylvaline;

N-{3-bromo-2-[2'-(1H-tetrazol-5-yl)-phenyl]-5-ylmethylbenzothiophene}-N-cyclopropylcarbonylvaline;

N-{3-bromo-2-[2'-(1H-tetrazol-5-yl)-phenyl]-5-ylmethylbenzothiophene}-N-cyclopropylmethylcarbonylvaline;

N-{3-bromo-2-[2'-(1H-tetrazol-5-yl)-phenyl]-5-ylmethylindole}-N-butyrylvaline;

N-{3-bromo-2-[2'-(1H-tetrazol-5-yl)-phenyl]-5-ylmethylindole}-N-caproylvaline;

N-{3-bromo-2-[2'-(1H-tetrazol-5-yl)-phenyl]-5-ylmethylindole}-N-propionylvaline;

N-{3-bromo-2-[2'-(1H-tetrazol-5-yl)-phenyl]-5-ylmethylindole}-N-ethoxycarbonylvaline;

N-{3-bromo-2-[2'-(1H-tetrazol-5-yl)-phenyl]-5-ylmethylindole}-N-propoxycarbonylvaline;

N-{3-bromo-2-[2'-(1H-tetrazol-5-yl)-phenyl]-5-ylmethylindole}-N-cyclopropoxycarbonylvaline;

N-{3-bromo-2-[2'-(1H-tetrazol-5-yl)-phenyl]-5-ylmethylindole}-N-cyclopentylcarbonylvaline;

N-{3-bromo-2-[2'-(1H-tetrazol-5-yl)-phenyl]-5-ylmethylindole}-N-cyclopropylcarbonylvaline;

N-{3-bromo-2-[2'-(1H-tetrazol-5-yl)-phenyl]-5-ylmethylindole}-N-cyclopropylmethylcarbonylvaline;

N-{3-bromo-2-[2'-(1H-tetrazol-5-yl)-phenyl]-5-ylmethylbenzofuran}-N-butyrylalanine;

N-{3-bromo-2-[2'-(1H-tetrazol-5-yl)-phenyl]-5-ylmethylbenzofuran}-N-caproylalanine;

N-{3-bromo-2-[2'-(1H-tetrazol-5-yl)-phenyl]-5-ylmethylbenzofuran}-N-propionylalanine;

N-{3-bromo-2-[2'-(1H-tetrazol-5-yl)-phenyl]-5-ylmethylbenzofuran}-N-ethoxycarbonylalanine;

N-{3-bromo-2-[2'-(1H-tetrazol-5-yl)-phenyl]-5-ylmethylbenzofuran}-N-propoxycarbonylalanine;

N-{3-bromo-2-[2'-(1H-tetrazol-5-yl)-phenyl]-5-ylmethylbenzofuran}-N-cyclopropoxycarbonylvaline;

N-{3-bromo-2-[2'-(1H-tetrazol-5-yl)-phenyl]-5-ylmethylbenzofuran}-N-cyclopentylcarbonylalanine;

N-{3-bromo-2-[2'-(1H-tetrazol-5-yl)-phenyl]-5-ylmethylbenzofuran}-N-cyclopropylcarbonylalanine;

N-{3-bromo-2-[2'-(1H-tetrazol-5-yl)-phenyl]-5-ylmethylbenzofuran}-N-cyclopropylmethylcarbonylalanine;

N-{3-bromo-2-[2'-(1H-tetrazol-5-yl)-phenyl]-5-ylmethylbenzofuran}-N-butyrylalanine;

N-{3-bromo-2-[2'-(1H-tetrazol-5-yl)-phenyl]-5-ylmethylbenzofuran}-N-caproylalanine;

N-{3-bromo-2-[2'-(1H-tetrazol-5-yl)-phenyl]-5-ylmethylbenzofuran}-N-propionylalanine;

N-{3-bromo-2-[2'-(1H-tetrazol-5-yl)-phenyl]-5-ylmethylbenzofuran}-N-ethoxycarbonylalanine;

N-{3-bromo-2-[2'-(1H-tetrazol-5-yl)-phenyl]-5-ylmethylbenzofuran}-N-propoxycarbonylalanine;

N-{3-bromo-2-[2'-(1H-tetrazol-5-yl)-phenyl]-5-ylmethylbenzofuran}-N-cyclopropoxycarbonylalanine;

N-{3-bromo-2-[2'-(1H-tetrazol-5-yl)-phenyl]-5-ylmethylbenzofuran}-N-cyclopentylcarbonylalanine;

N-{3-bromo-2-[2'-(1H-tetrazol-5-yl)-phenyl]-5-ylmethylbenzofuran}-N-cyclopropylcarbonylalanine;

N-{3-bromo-2-[2'-(1H-tetrazol-5-yl)-phenyl]-5-ylmethylbenzofuran}-N-cyclopropylmethylcarbonylalanine;

N-{3-bromo-2-[2'-(1H-tetrazol-5-yl)-phenyl]-5-ylmethylindole}-N-butyrylalanine;

N-{3-bromo-2-[2'-(1H-tetrazol-5-yl)-phenyl]-5-ylmethylindole}-N-caproylalanine;

N-{3-bromo-2-[2'-(1H-tetrazol-5-yl)-phenyl]-5-ylmethylindole}-N-propionylalanine;

N-{3-bromo-2-[2'-(1H-tetrazol-5-yl)-phenyl]-5-ylmethylindole}-N-ethoxycarbonylalanine;

N-{3-bromo-2-[2'-(1H-tetrazol-5-yl)-phenyl]-5-ylmethylindole}-N-propoxycarbonylalanine;

N-{3-bromo-2-[2'-(1H-tetrazol-5-yl)-phenyl]-5-ylmethylindole}-N-cyclopropoxycarbonylalanine;

N-{3-bromo-2-[2'-(1H-tetrazol-5-yl)-phenyl]-5-ylmethylindole}-N-cyclopentylcarbonylalanine;

N-{3-bromo-2-[2'-(1H-tetrazol-5-yl)-phenyl]-5-ylmethylindole}-N-cyclopropylcarbonylalanine;

N-{3-bromo-2-[2'-(1H-tetrazol-5-yl)-phenyl]-5-ylmethylindole}-N-cyclopropylmethylcarbonylalanine;

N-[2-(2'-tetrazol-5-yl)-phenyl)-quinolin-6-ylmethyl]-N-butyryl-1-aminomethylcyclohexane-1-carboxylic acid; $R_f$=0.35 ($CH_2Cl_2/CH_3OH$=4:1);

N-[2-(2'-tetrazol-5-yl)-phenyl)-quinolin-6-ylmethyl]-N-valeroyl-1-aminomethylcyclohexane-1-carboxylic acid; $R_f$=0.26 ($CH_2Cl_2/CH_3OH$=4:1);

N-[2-(2'-tetrazol-5-yl)-phenyl)-quinolin-6-ylmethyl]-N-butyryl-1-aminomethylcyclopentane-1-carboxylic acid;

N-[2-(2'-tetrazol-5-yl)-phenyl)-quinolin-6-ylmethyl]-N-caproyl-1-aminomethylcyclopentane-1-carboxylic acid;

N-[2-(2'-tetrazol-5-yl)-phenyl)-quinolin-6-ylmethyl]-N-propionyl-1-aminomethylcyclopentane-1-carboxylic acid;

N-[2-(2'-tetrazol-5-yl)-phenyl)-quinolin-6-ylmethyl]-N-ethoxycarbonyl-1-aminomethylcyclopentane-1-carboxylic acid;

N-[2-(2'-tetrazol-5-yl)-phenyl)-quinolin-6-ylmethyl]-N-propoxycarbonyl-1-aminomethylcyclopentane-1-carboxylic acid;

N-[2-(2'-tetrazol-5-yl)-phenyl)-quinolin-6-ylmethyl]-N-cyclopropoxycarbonyl-1-aminomethylcyclopentane-1-carboxylic acid;

N-[2-(2'-tetrazol-5-yl)-phenyl)-quinolin-6-ylmethyl]-N-cyclopropylcarbonyl-1-aminomethylcyclopentane-1-carboxylic acid;

N-[2-(2'-tetrazol-5-yl)-phenyl)-quinolin-6-ylmethyl]-N-cyclopentylcarbonyl-1-aminomethylcyclopentane-1-carboxylic acid;

N-[2-(2'-tetrazol-5-yl)-phenyl)-quinolin-6-ylmethyl]-N-cyclopropylmethylcarbonyl-1-aminomethylcyclopentane-1-carboxylic acid;

N-[2-(2'-carboxyphenyl)-quinolin-6-ylmethyl]-N-butyryl-1-aminomethylcyclopentane-1-carboxylic acid;

N-[2-(2'-carboxyphenyl)-quinolin-6-ylmethyl]-N-caproyl-1-aminomethylcyclopentane-1-carboxylic acid;

N-[2-(2'-carboxyphenyl)-quinolin-6-ylmethyl]-N-propionyl-1-aminomethylcyclopentane-1-carboxylic acid;

N-[2-(2'-carboxyphenyl)-quinolin-6-ylmethyl]-N-ethoxycarbonyl-1-aminomethylcyclopentane-1-carboxylic acid;

N-[2-(2'-carboxyphenyl)-quinolin-6-ylmethyl]-N-propoxy-carbonyl-1-aminomethylcyclopentane-1-carboxylic acid;

N-[2-(2'-carboxyphenyl)-quinolin-6-ylmethyl]-N-cyclopropoxycarbonyl-1-aminomethylcyclopentane-1-carboxylic acid;

N-[2-(2'-carboxyphenyl)-quinolin-6-ylmethyl]-N-cyclopropylcarbonyl-1-aminomethylcyclopentane-1-carboxylic acid;

N-[2-(2'-carboxyphenyl)-quinolin-6-ylmethyl]-N-cyclopentylcarbonyl-1-aminomethylcyclopentane-1-carboxylic acid;

N-[2-(2'-carboxyphenyl)-quinolin-6-ylmethyl]-N-cyclopropylmethylcarbonyl-1-aminomethylcyclopentane-1-carboxylic acid;

N-[2-(2'-tetrazol-5-yl)-phenyl)-naphthalen-6-ylmethyl]-N-butyryl-1-aminomethylcyclopentane-1-carboxylic acid;

N-[2-(2'-tetrazol-5-yl)-phenyl)-naphthalen-6-ylmethyl]-N-caproyl-1-aminomethylcyclopentane-1-carboxylic acid;

N-[2-(2'-tetrazol-5-yl)-phenyl)-naphthalen-6-ylmethyl]-N-propionyl-1-aminomethylcyclopentane-1-carboxylic acid;

N-[2-(2'-tetrazol-5-yl)-phenyl)-naphthalen-6-ylmethyl]-N-ethoxycarbonyl-1-aminomethylcyclopentane-1-carboxylic acid;

N-[2-(2'-tetrazol-5-yl)-phenyl)-naphthalen-6-ylmethyl]-N-propoxycarbonyl-1-aminomethylcyclopentane-1-carboxylic acid;

N-[2-(2'-tetrazol-5-yl)-phenyl)-naphthalen-6-ylmethyl]-N-cyclopropoxycarbonyl-1-aminomethylcyclopentane-1-carboxylic acid;

N-[2-(2'-tetrazol-5-yl)-phenyl)-naphthalen-6-ylmethyl]-N-cyclopropylcarbonyl-1-aminomethylcyclopentane-1-carboxylic acid;

N-[2-(2'-tetrazol-5-yl)-phenyl)-naphthalen-6-ylmethyl]-N-cyclopentylcarbonyl-1-aminomethylcyclopentane-1-carboxylic acid;

N-[2-(2'-tetrazol-5-yl)-phenyl)-naphthalen-6-ylmethyl]-N-cyclopropylmethylcarbonyl-1-aminomethylcyclopentane-1-carboxylic acid;

N-[2-(2'-carboxyphenyl)-naphthalen-6-ylmethyl]-N-butyryl-1-aminomethylcyclopentane-1-carboxylic acid;

N-[2-(2'-carboxyphenyl)-naphthalen-6-ylmethyl]-N-caproyl-1-aminomethylcyclopentane-1-carboxylic acid;

N-[2-(2'-carboxyphenyl)-naphthalen-6-ylmethyl]-N-propionyl-1-aminomethylcyclopentane-1-carboxylic acid;

N-[2-(2'-carboxyphenyl)-naphthalen-6-ylmethyl]-N-ethoxycarbonyl-1-aminomethylcyclopentane-1-carboxylic acid;

N-[2-(2'-carboxyphenyl)-naphthalen-6-ylmethyl]-N-propoxycarbonyl-1-aminomethylcyclopentane-1-carboxylic acid;

N-[2-(2'-carboxyphenyl)-naphthalen-6-ylmethyl]-N-cyclopropoxycarbonyl-1-aminomethylcyclopentane-1-carboxylic acid;

N-[2-(2'-carboxyphenyl)-naphthalen-6-ylmethyl]-N-cyclopropylcarbonyl-1-aminomethylcyclopentane-1-carboxylic acid;

N-[2-(2'-carboxyphenyl)-naphthalen-6-ylmethyl]-N-cyclopentylcarbonyl-1-aminomethylcyclopentane-1-carboxylic acid;

N-[2-(2'-carboxyphenyl)-naphthalen-6-ylmethyl]-N-cyclopropylmethylcarbonyl-1-aminomethylcyclopentane-1-carboxylic acid;

N-[2-(2'-(tetrazol-5-yl)-phenyl)-quinolin-6-ylmethyl]-N-butyrylvaline;

N-[2-(2'-(tetrazol-5-yl)-phenyl)-quinolin-6-ylmethyl]-N-caproylvaline;

N-[2-(2'-(tetrazol-5-yl)-phenyl)-quinolin-6-ylmethyl]-N-propionylvaline;

N-[2-(2'-(tetrazol-5-yl)-phenyl)-quinolin-6-ylmethyl]-N-ethoxycarbonylvaline;

N-[2-(2'-(tetrazol-5-yl)-phenyl)-quinolin-6-ylmethyl]-N-propoxycarbonylvaline;

N-[2-(2'-(tetrazol-5-yl)-phenyl)-quinolin-6-ylmethyl]-N-cyclopropoxycarbonylvaline;

N-[2-(2'-(tetrazol-5-yl)-phenyl)-quinolin-6-ylmethyl]-N-cyclopropylcarbonylvaline;

N-[2-(2'-(tetrazol-5-yl)-phenyl)-quinolin-6-ylmethyl]-N-cyclopentylcarbonylvaline;

N-[2-(2'-(tetrazol-5-yl)-phenyl)-quinolin-6-ylmethyl]-N-cyclopropylmethylcarbonyl;

N-[2-(2'-carboxyphenyl)-quinolin-6-ylmethyl]-N-butyrylvaline;

N-[2-(2'-carboxyphenyl)-quinolin-6-ylmethyl]-N-caproylvaline;

N-[2-(2'-carboxyphenyl)-quinolin-6-ylmethyl]-N-propionylvaline;

N-[2-(2'-carboxyphenyl)-quinolin-6-ylmethyl]-N-ethoxycarbonylvaline;

N-[2-(2'-carboxyphenyl)-quinolin-6-ylmethyl]-N-propoxycarbonylvaline;

N-[2-(2'-carboxyphenyl)-quinolin-6-ylmethyl]-N-cyclopropoxycarbonylvaline;

N-[2-(2'-carboxyphenyl)-quinolin-6-ylmethyl]-N-cyclopropylcarbonylvaline;

N-[2-(2'-carboxyphenyl)-quinolin-6-ylmethyl]-N-cyclopentylcarbonylvaline;

N-[2-(2'-carboxyphenyl)-quinolin-6-ylmethyl]-N-cyclopropylmethylcarbonylvaline;

N-[2-(2'-(tetrazol-5-yl)-phenyl)-naphthalen-6-ylmethyl]-N-butyrylvaline;

N-[2-(2'-(tetrazol-5-yl)-phenyl)-naphthalen-6-ylmethyl]-N-caproylvaline;

N-[2-(2'-(tetrazol-5-yl)-phenyl)-naphthalen-6-ylmethyl]-N-propionylvaline;

N-[2-(2'-(tetrazol-5-yl)-phenyl)-naphthalen-6-ylmethyl]-N-ethoxycarbonylvaline;

N-[2-(2'-(tetrazol-5-yl)-phenyl)-naphthalen-6-ylmethyl]-N-propoxycarbonylvaline;

N-[2-(2'-(tetrazol-5-yl)-phenyl)-naphthalen-6-ylmethyl]-N-cyclopropoxycarbonylvaline;

N-[2-(2'-(tetrazol-5-yl)-phenyl)-naphthalen-6-ylmethyl]-N-cyclopropylcarbonylvaline;

N-[2-(2'-(tetrazol-5-yl)-phenyl)-naphthalen-6-ylmethyl]-N-cyclopentylcarbonylvaline;

N-[2-(2'-(tetrazol-5-yl)-phenyl)-naphthalen-6-ylmethyl]-N-cyclopropylmethylcarbonylvaline;

N-[2-(2'-(carboxyphenyl)-naphthalen-6-ylmethyl]-N-butyrylvaline;

N-[2-(2'-(carboxyphenyl)-naphthalen-6-ylmethyl]-N-caproylvaline;

N-[2-(2'-(carboxyphenyl)-naphthalen-6-ylmethyl]-N-propionylvaline;

N-[2-(2'-(carboxyphenyl)-naphthalen-6-ylmethyl]-N-ethoxycarbonylvaline;

N-[2-(2'-(carboxyphenyl)-naphthalen-6-ylmethyl]-N-propoxycarbonylvaline;

N-[2-(2'-(carboxyphenyl)-naphthalen-6-ylmethyl]-N-cyclopropoxycarbonylvaline;

N-[2-(2'-(carboxyphenyl)-naphthalen-6-ylmethyl]-N-cyclopropylcarbonylvaline;

N-[2-(2'-(carboxyphenyl)-naphthalen-6-ylmethyl]-N-cyclopentylcarbonylvaline;

N-[2-(2'-(carboxyphenyl)-naphthalen-6-ylmethyl]-N-cyclopropylmethylcarbonylvaline;

N-[2-(2'-(tetrazol-5-yl)-phenyl)-quinolin-6-ylmethyl]-N-butyrylalanine;

N-[2-(2'-(tetrazol-5-yl)-phenyl)-quinolin-6-ylmethyl]-N-caproylalanine;

N-[2-(2'-(tetrazol-5-yl)-phenyl)-quinolin-6-ylmethyl]-N-propionylalanine;

N-[2-(2'-(tetrazol-5-yl)-phenyl)-quinolin-6-ylmethyl]-N-ethoxycarbonylalanine;

N-[2-(2'-(tetrazol-5-yl)-phenyl)-quinolin-6-ylmethyl]-N-propoxycarbonylalanine;

N-[2-(2'-(tetrazol-5-yl)-phenyl)-quinolin-6-ylmethyl]-N-cyclopropoxycarbonylalanine;

N-[2-(2'-(tetrazol-5-yl)-phenyl)-quinolin-6-ylmethyl]-N-cyclopropylcarbonylalanine;

N-[2-(2'-(tetrazol-5-yl)-phenyl)-quinolin-6-ylmethyl]-N-cyclopentylcarbonylalanine;

N-[2-(2'-(tetrazol-5-yl)-phenyl)-quinolin-6-ylmethyl]-N-cyclopropylmethylcarbonylalanine;

N-[2-(2'-(carboxyphenyl)-quinolin-6-ylmethyl]-N-butyrylalanine;

N-[2-(2'-(carboxyphenyl)-quinolin-6-ylmethyl]-N-caproylalanine;

N-[2-(2'-(carboxyphenyl)-quinolin-6-ylmethyl]-N-propionylalanine;

N-[2-(2'-(carboxyphenyl)-quinolin-6-ylmethyl]-N-ethoxycarbonylalanine;

N-[2-(2'-(carboxyphenyl)-quinolin-6-ylmethyl]-N-propoxycarbonylalanine;

N-[2-(2'-(carboxyphenyl)-quinolin-6-ylmethyl]-N-cyclopropoxycarbonylalanine;

N-[2-(2'-(carboxyphenyl)-quinolin-6-ylmethyl]-N-cyclopropylcarbonylalanine;

N-[2-(2'-(carboxyphenyl)-quinolin-6-ylmethyl]-N-cyclopentylcarbonylalanine;

N-[2-(2'-(carboxyphenyl)-quinolin-6-ylmethyl]-N-cyclopropylmethylcarbonylalanine;

N-[2-(2'-(tetrazol-5-yl)-phenyl)-naphthalen-6-ylmethyl]-N-butyrylalanine; $R_f$=0.075 (CH$_2$Cl$_2$/CH$_3$OH=4:1);

N-[2-(2'-(tetrazol-5-yl)-phenyl)-naphthalen-6-ylmethyl]-N-caproylalanine;

N-[2-(2'-(tetrazol-5-yl)-phenyl)-naphthalen-6-ylmethyl]-N-propionylalanine;

N-[2-(2'-(tetrazol-5-yl)-phenyl)-naphthalen-6-ylmethyl]-N-ethoxycarbonylalanine;

N-[2-(2'-(tetrazol-5-yl)-phenyl)-naphthalen-6-ylmethyl]-N-propoxycarbonylalanine;

N-[2-(2'-(tetrazol-5-yl)-phenyl)-naphthalen-6-ylmethyl]-N-cyclopropoxycarbonylalanine;

N-[2-(2'-(tetrazol-5-yl)-phenyl)-naphthalen-6-ylmethyl]-N-cyclopropylcarbonylalanine;

N-[2-(2'-(tetrazol-5-yl)-phenyl)-naphthalen-6-ylmethyl]-N-cyclopentylcarbonylalanine;

N-[2-(2'-(tetrazol-5-yl)-phenyl)-naphthalen-6-ylmethyl]-N-cyclopropylmethylcarbonylalanine;

N-[2-(2'-carboxyphenyl)-naphthalen-6-ylmethyl]-N-butyrylalanine;

N-[2-(2'-carboxyphenyl)-naphthalen-6-ylmethyl]-N-caproylalanine;

N-[2-(2'-carboxyphenyl)-naphthalen-6-ylmethyl]-N-propionylalanine;

N-[2-(2'-carboxyphenyl)-naphthalen-6-ylmethyl]-N-ethoxycarbonylalanine;

N-[2-(2'-carboxyphenyl)-naphthalen-6-ylmethyl]-N-propoxycarbonylalanine;

N-[2-(2'-carboxyphenyl)-naphthalen-6-ylmethyl]-N-cyclopropoxycarbonylalanine;

N-[2-(2'-carboxyphenyl)-naphthalen-6-ylmethyl]-N-cyclopropylcarbonylalanine;

N-[2-(2'-carboxyphenyl)-naphthalen-6-ylmethyl]-N-cyclopentylcarbonylalanine;

N-[2-(2'-carboxyphenyl)-naphthalen-6-ylmethyl]-N-cyclopropylmethylcarbonylalanine;

EXAMPLE 24

Tablets, each comprising 50 mg of active ingredient, for example N-[2-(2-(1H-tetrazol-5-yl)-phenyl)-quinolin-6-ylmethyl]-N-valeroyl-1-aminomethylcyclopentane-1-carboxylic acid, can be prepared as follows:

| Composition (for 10 000 tablets): | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch. The mixture is moistened with an alcoholic solution of the gelatin and granulated through a sieve. After drying, the remainder of the potato starch, the talc, the magnesium stearate and the highly dispersed silica are added and the mixture is compressed to form tablets each weighing 145.0 mg and each comprising 50.0 mg of active ingredient, which may, if desired, be provided with dividing notches for finer adaptation of the dose.

EXAMPLE 25

Film-coated tablets, each comprising 100 mg of active ingredient, for example N-[2-(2-(1H-tetrazol-5-yl)-phenyl)-quinolin-6-ylmethyl]-N-valeroyl-1-aminomethylcyclopentane-1-carboxylic acid, can be prepared as follows:

| Composition (for 1000 tablets): | |
|---|---|
| active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed and moistened with a paste prepared from 15 g of corn starch and water (with heating), and granulated. The granules are dried, and the remainder of the corn starch, the talc and the calcium stearate are added and mixed with the granules. The mixture is compressed to form tablets (weight: 280 mg) which are film-coated with a solution of the hydroxypropylmethyl-cellulose and the shellac in dichloromethane (final weight of the film-coated tablet: 283 mg).

EXAMPLE 26

In an analogous manner to that described in Examples 24 and 25, it is also possible to prepare tablets and film-coated tablets that comprise a different compound of formula I or a pharmaceutically acceptable salt of a compound of formula I, for example according to any one of Examples 1 to 23.

What is claimed is:

1. A compound of the formula

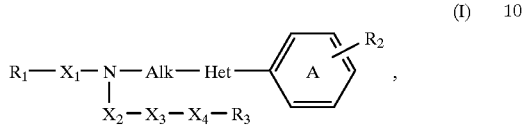

wherein $R_1$ is $C_1$–$C_7$alkyl that is unsubstituted or substituted by halogen of by hydroxy, or is $C_2$–$C_7$-alkenyl, $C_3$–$C_7$cycloalkyl, $C_3$–$C_7$cycloalkoxy, $C_1$–$C_7$-alkoxy or $C_3$–$C_7$cycloalkyl-$C_1$–$C_7$-alkoxy;

$R_2$ is 1H-tetrazol-5-yl;

$R_3$ is 1H-tetrazol-5-yl, hydroxymethyl, $C_1$–$C_7$alkoxymethyl, formyl, carboxy, $C_1$–$C_7$-alkoxycarbonyl, $C_1$–$C_4$alkoxy-$C_1$–$C_7$alkoxycarbonyl, phenyl-$C_1$–$C_4$alkoxycarbonyl, or carbamoyl, the amino group of which is unsubstituted or mono-substituted by $C_1$–$C_7$alkyl, $C_3$–$C_7$alkenyl or by phenyl-$C_1$–$C_7$alkyl or di-substituted by $C_1$–$C_7$alkyl, $C_3$–$C_7$alkenyl or by phenyl-$C_1$–$C_7$alkyl independently of one another, or is di-substituted by $C_2$–$C_7$alkylene or by $C_2$–$C_4$alkyleneoxy-$C_2C_4$alkylene;

Alk is methylene, ethylene or ethylidene;

Het is

wherein $Y_2$ and $Y_3$ are each C(R'); and R' is hydrogen, halogen, $C_1$–$C_7$alkyl, $C_1$–$C_7$-alkoxy, $C_2$–$C_7$alkenyloxy, phenoxy, benzyloxy, trifluoromethyl or $S(O)_m$—R, wherein m is 0, 1 or 2; and R is hydrogen or $C_1$–$C_7$alkyl;

$X_1$ is —CO—;

$X_2$ is a bond;

$X_4$ is a bond;

$X_3$ is the structural element —$C(X_a)(X_b)$— and $X_a$ is hydrogen or $C_1$–$C_7$alkyl and $X_b$ is $C_1$–$C_7$alkyl;

and the rings A, A' and D, with the exception of the substituents indicated in the formula, and also aromatic substituents are, independently of one another, unsubstituted or mono- or poly-substituted by substituents selected from the group consisting of halogen, $C_1$–$C_7$-alkyl, $C_1$–$C_7$alkoxy, $C_2$–$C_7$alkenyloxy, phenoxy, benzyloxy, trifluoromethyl and $S(O)_m$—R, wherein m is 0, 1 or 2 and R is hydrogen or $C_1$–$C_7$alkyl;

or a salt thereof.

2. A compound according to claim 1 of formula I, wherein $R_1$ is $C_1$–$C_7$alkyl that is unsubstituted or substituted by halogen or by hydroxy, or is $C_2$–$C_7$-alkenyl, $C_3$–$C_7$-cycloalkyl or $C_1$–$C_7$alkoxy; or a salt thereof.

3. A compound according to claim 1 of formula I, wherein $R_1$ is $C_2$–$C_7$alkyl or is $C_1$–$C_7$alkyl that is substituted by halogen or by hydroxy, or is $C_3$–$C_7$-alkenyl, $C_3$–$C_6$cycloalkyl or $C_1$–$C_7$alkoxy;

$R_2$ is 1H-tetrazol-5-yl;

$R_3$ is 1H-tetrazol-5-yl, hydroxymethyl, $C_1$–$C_7$alkoxymethyl, formyl, carboxy, $C_1$–$C_4$-alkoxycarbonyl, $C_1$–$C_4$alkoxy-$C_1$–$C_4$alkoxycarbonyl, phenyl-$C_1$–$C_4$alkoxycarbonyl or carbamoyl, the amino group of which is mono-substituted by $C_1$–$C_4$alkyl or di-substituted by $C_1$–$C_4$alkyl groups which may be the same or different, or is di-substituted by $C_4$–$C_6$-alkylene or by ethyleneoxyethylene;

Alk is methylene, ethylene or ethylidene;

Het is

wherein $Y_2$ and $Y_3$ are each CH;

$X_1$ is —CO—;

each of the variables $X_2$ and $X_4$ is a bond;

$X_3$ is the structural element —$C(X_a)(X_b)$— and $X_a$ is hydrogen or $C_1$–$C_7$alkyl and $X_b$ is $C_1$–$C_7$alkyl;

and the rings A, A' and D, with the exception of the substituents indicated in the formula, and also aromatic substituents are, independently of one another, unsubstituted or mono- or poly-substituted by substituents selected from the group consisting of halogen, $C_1$–$C_4$-alkyl, $C_1$–$C_4$alkoxy, $C_3$–$C_5$alkenyloxy, phenoxy, benzyloxy, trifluoromethyl and $S(O)_m$—R, wherein m is 0, 1 or 2 and R is hydrogen or $C_1$–$C_4$alkyl;

or a salt thereof.

4. A compound according to claim 2 of formula I, wherein $R_1$ is $C_2$–$C_7$alkyl or is $C_1$–$C_4$alkyl that is substituted by halogen or by hydroxy, or is $C_3$–$C_7$-alkenyl, $C_3$–$C_6$cycloalkyl or $C_1$–$C_7$alkoxy;

$R_2$ is 1H-tetrazol-5-yl;

$R_3$ is 1H-tetrazol-5-yl, carboxy, $C_1$–$C_4$alkoxycarbonyl, $C_1$–$C_4$alkoxy-$C_1$–$C_4$-alkoxycarbonyl, or phenyl-$C_1$–$C_2$alkoxycarbonyl;

Alk is methylene, ethylene or ethylidene;

Het is

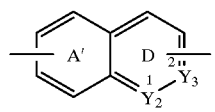

wherein each of the variables $Y_2$ and $Y_3$ is CH;

each of the variables $X_2$ and $X_4$ is a bond;

$X_3$ is the structural element —$C(X_a)(X_b)$— and $X_a$ is hydrogen or $C_1$–$C_5$alkyl and $X_b$ is $C_1$–$C_5$alkyl;

and the rings A, A' and D, with the exception of the substituents indicated in the formula, are, independently of one another, unsubstituted or mono- or poly-substituted by substituents selected from the group consisting of halogen, $C_1$–$C_4$-alkyl, $C_1$–$C_4$alkoxy, and trifluoromethyl;

or a salt thereof.

5. A compound according to claim 1 of formula I, wherein each of the variables $Y_2$ and $Y_3$ is C(R') wherein R' is halogen, $C_1$–$C_4$alkyl, $C_1$–$C_4$alkoxy or trifluoromethyl, or a salt thereof.

6. A compound according to claim 1 of formula I, wherein
R$_1$ is C$_2$–C$_7$alkyl or C$_1$–C$_4$alkoxy;
R$_2$ is 1H-tetrazol-5-yl;
R$_3$ is carboxy or C$_1$–C$_4$alkoxycarbonyl;
Alk is methylene;
Het is

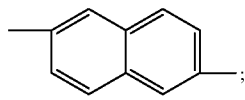

X$_1$ is —CO—;
each of X$_2$ and X$_4$ is a bond; and X$_3$ is the structural element —C(X$_a$)(X$_b$)— and X$_a$ is hydrogen or C$_1$–C$_5$alkyl and X$_b$ is C$_1$–C$_5$alkyl;
or a salt thereof.

7. A compound according to claim 2 of formula I, wherein R$_3$ is hydroxymethyl, C$_1$–C$_4$alkoxymethyl or formyl; the other variables are as defined above in each case.

8. A compound according to claim 1 of formula I, wherein
R$_1$ is C$_2$–C$_5$alkyl;
R$_2$ is 1H-tetrazol-5-yl;
R$_3$ is carboxy or C$_1$–C$_4$alkoxycarbonyl;
Alk is methylene;
Het is

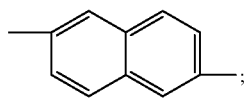

X$_1$ is —CO—;
each of X$_2$ and X$_4$ is a bond; and X$_3$ is the structural element —C(X$_a$)(X$_b$)— and X$_a$ is hydrogen or C$_1$–C$_5$alkyl and X$_b$ is C$_1$–C$_5$alkyl;
or a salt thereof.

9. A compound of claim 1 selected from the group consisting of
N-[2-(2'-(1H-tetrazol-5-yl)-phenyl)-naphthalene-6-ylmethyl]-N-valeroylvaline;
N-[2-(2'-(1H-tetrazol-5-yl)-phenyl)-naphthalene-6-ylmethyl]-N-valeroyl-1-aminomethyl-cyclopentane-1-carboxyl acid;
N-[2-(2'-(1H-tetrazol-5-yl)-phenyl)-naphthalene-6-ylmethyl]-N-valeroyl-2-aminomethyl-2-ethylbutyric acid; or
N-[2-(2'-(1H-tetrazol-5-yl)-phenyl)-naphthalene-6-ylmethyl]-N-valeroyl-1-aminomethyl-cyclohexane-1-carboxylic acid;
or a salt thereof.

10. A compound according to claim 1 selected from the group consisting of
N-[2-(2'-(1H-tetrazol-5-yl)-phenyl)-naphthalene-6-ylmethyl]-N-valeroyl-1-aminomethyl-cyclopentane-1-carboxylic acid ethyl ester;
N-[2-(2'-(1H-tetrazol-5-yl)-phenyl)-naphthalene-6-ylmethyl]-N-valeroyl-3-amino-2,2-dimethylpropionic acid; and
N-[2-(2'-(1H-tetrazol-5-yl)-phenyl)-naphthalene-6-ylmethyl]-N-butyrylvaline;
or a salt thereof.

11. A pharmaceutical composition comprising an antihypertensively effective amount of a compound according to claim 1 or a pharmaceutically acceptable salt thereof, if appropriate in addition to customary pharmaceutical adjuncts.

12. A method for the treatment of high blood pressure, cardiac insufficiency or glaucoma in a subject in need of such treatment, comprising administering to such subject an amount effective for the treatment of high blood pressure, cardiac insufficiency or glaucoma of a compound according to claim 1 or a pharmaceutically acceptable salt thereof.

* * * * *